(12) United States Patent
Shih et al.

(10) Patent No.: US 9,771,625 B2
(45) Date of Patent: Sep. 26, 2017

(54) MONOAMINE OXIDASE INHIBITORS AND METHODS FOR TREATMENT AND DIAGNOSIS OF PROSTATE CANCER

(75) Inventors: Jean C. Shih, Beverly Hills, CA (US); Leland Chung, Los Angeles, CA (US); Haiyen E. Zhau, Los Angeles, CA (US); Boyang Jason Wu, Los Angeles, CA (US); Bogdan Z. Olenyuk, Sierra Madre, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 25 days.

(21) Appl. No.: 13/559,431

(22) Filed: Jul. 26, 2012

(65) Prior Publication Data
US 2013/0039854 A1 Feb. 14, 2013

Related U.S. Application Data

(60) Provisional application No. 61/511,920, filed on Jul. 26, 2011.

(51) Int. Cl.
| | |
|---|---|
| *A61K 31/405* | (2006.01) |
| *A61K 31/352* | (2006.01) |
| *A61K 31/357* | (2006.01) |
| *A61K 31/381* | (2006.01) |
| *C12N 15/113* | (2010.01) |
| *A61K 31/366* | (2006.01) |
| *A61K 31/5375* | (2006.01) |
| *A61K 31/713* | (2006.01) |
| *A61K 47/48* | (2006.01) |
| *A61K 49/00* | (2006.01) |

(52) U.S. Cl.
CPC .... *C12Y 104/03004* (2013.01); *A61K 31/352* (2013.01); *A61K 31/357* (2013.01); *A61K 31/366* (2013.01); *A61K 31/381* (2013.01); *A61K 31/405* (2013.01); *A61K 31/5375* (2013.01); *A61K 31/713* (2013.01); *A61K 47/48061* (2013.01); *A61K 49/0032* (2013.01); *C12N 15/1137* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 7,056,952 | B1 | 6/2006 | Joannou |
| 7,344,699 | B2 * | 3/2008 | Lappin et al. ............... 424/1.41 |
| 7,799,955 | B2 | 9/2010 | Joannou |
| 2005/0222248 | A1 | 10/2005 | Joannou |
| 2008/0125481 | A1 | 5/2008 | Joannou |
| 2009/0209655 | A1 | 8/2009 | Joannou |
| 2010/0048921 | A1 | 2/2010 | Gorne et al. |
| 2010/0137425 | A1 | 6/2010 | Bergan et al. |
| 2010/0273891 | A1 | 10/2010 | Joannou |
| 2010/0290997 | A1 | 11/2010 | Li et al. |

FOREIGN PATENT DOCUMENTS

| | | | |
|---|---|---|---|
| DE | 102007002386 A1 | | 7/2008 |
| WO | 0066576 A1 | | 11/2000 |
| WO | WO 2009012109 A2 | * | 1/2009 |
| WO | 2009152440 A1 | | 12/2009 |
| WO | 2010042933 A2 | | 4/2010 |
| WO | 2011116142 A1 | | 9/2011 |
| WO | 2012018761 A2 | | 2/2012 |

OTHER PUBLICATIONS

Yang et al. Clin Cancer Res 16(10) p. 2833-2844, May 15, 2010.*
Gao et al. Nature Biotechnology 22(6), p. 969-976, 2004.*
Samia et al. JACS 125(51)p. 15736-15737, 2003.*
Kukowska-Latallo et al. Cancer Res 65(12) p. 5317-5324, 2005.*
International search report and Written Opinion dated Feb. 13, 2013 issued in corresponding PCT application PCT/US2012/048407.
Peehl et al., "The Significance of Monoamine Oxidase-A Expression in High Grade Prostate Cancer" Journal of Urology, vol. 180, pp. 2206-2211, Nov. 2008. Flamand et al., "864 Monamine Oxidase A: A New Candidate Therapeutic Target for Advanced Prostate Cancer" European Urology Supplements, vol. 9, No. 2, p. 274, Apr. 1, 2010.
Flamand et al., "Targeting monoamine oxidase A in advanced prostate cancer" Journal of Cancer Research and Clinical Oncology, vol. 136, pp. 1761-1771, 2010.
Zhao et al., "Anti-oncogenic and pro-differentiation effects of clorgyline, a monoamine oxidase A inhibitor, on high grade prostate cancer cells" BMC Medical Genomics, vol. 2, pp. 1-15, 2009.
Partial international search report dated Nov. 27, 2012 issued in corresponding PCT application PCT/US2012/048407.
European Search Report (Communication pursuant to Rule 164(2)(b) and Article 94(3) EPC) dated Jul. 21, 2015 issued in corresponding EPC Application No. 12748805.4.

(Continued)

*Primary Examiner* — Nissa Westerberg
(74) *Attorney, Agent, or Firm* — DLA Piper LLP (US)

(57) ABSTRACT

A mechanism of monoamine oxidases (MAOs) driven epithelium-to-mesenchymal transition (EMT) is disclosed. Also disclosed are methods for treating cancer by inhibiting or suppressing MAOs in cancer cells. Novel MAOs inhibitors, such as small molecules, siRNA, shRNA, antisense oligonucleotides, aptamers, decoys, and pharmaceutical compositions useful for treating cancer by disrupting the workings of MAOs are provided. In particular, a class of conjugates formed by covalently conjugating near infrared dye 783, IR-780, and MHI-148 to a MAO inhibitor, such as clorgyline, with and without encapsulation it in a nanoparticle is provided. Other aspects of the invention include methods for forming the nano-conjugates, method for monitoring treatment progress in a cancer patient by monitoring the changes in MAO activity, methods for screening patients who are at risk of cancer or differentiating different forms of cancer by assaying the level and location of MAO activity.

3 Claims, 31 Drawing Sheets
(7 of 31 Drawing Sheet(s) Filed in Color)

(56) References Cited

OTHER PUBLICATIONS

Second Notification of Office Action dated Aug. 5, 2016 issued in counterpart Chinese patent application No. 201280046591.5.
Hyeran Lee et al., "Synthesis and Spectral Properties of Near-Infared Aminophenyl-, Hydroxyphenyl-, and Phenyl- Substituted Heptamethine Cyanines" Journal of Organic Chemistry, vol. 73, pp. 723-725, 2008.
CAS Registry Entry for 1147408-06-7, p. 1, Entered STN May 19, 2009.
International preliminary report on patentability dated Aug. 13, 2013 issued in corresponding PCT application PCT/US12/48407.

\* cited by examiner

| Day | WT MCP3 cells (# of tumors / # of injection sites) | MAOA-KD MCP3 cells (# of tumors / # of injection sites) |
|---|---|---|
| 1 | (0%) | (0%) |
| 11 | (16.67%) | (0%) |
| 13 | (41.67%) | (0%) |
| 15 | (50%) | (0%) |
| 19 | (54.17%) | (0%) |
| 23 | (62.5%) | (0%) |
| 25 | (70.83%) | (0%) |
| 27 | (79.17%) | (0%) |
| 29 | (87.5%) | (0%) |

Step 1: create an active amine group on dye

Step 2: Introduce a –COOH group on docetaxel

Step 3: conjugation of dye and docetaxel

S4s-I1-E4cCl-Suc-docetaxel
(also called IR-MUT1)

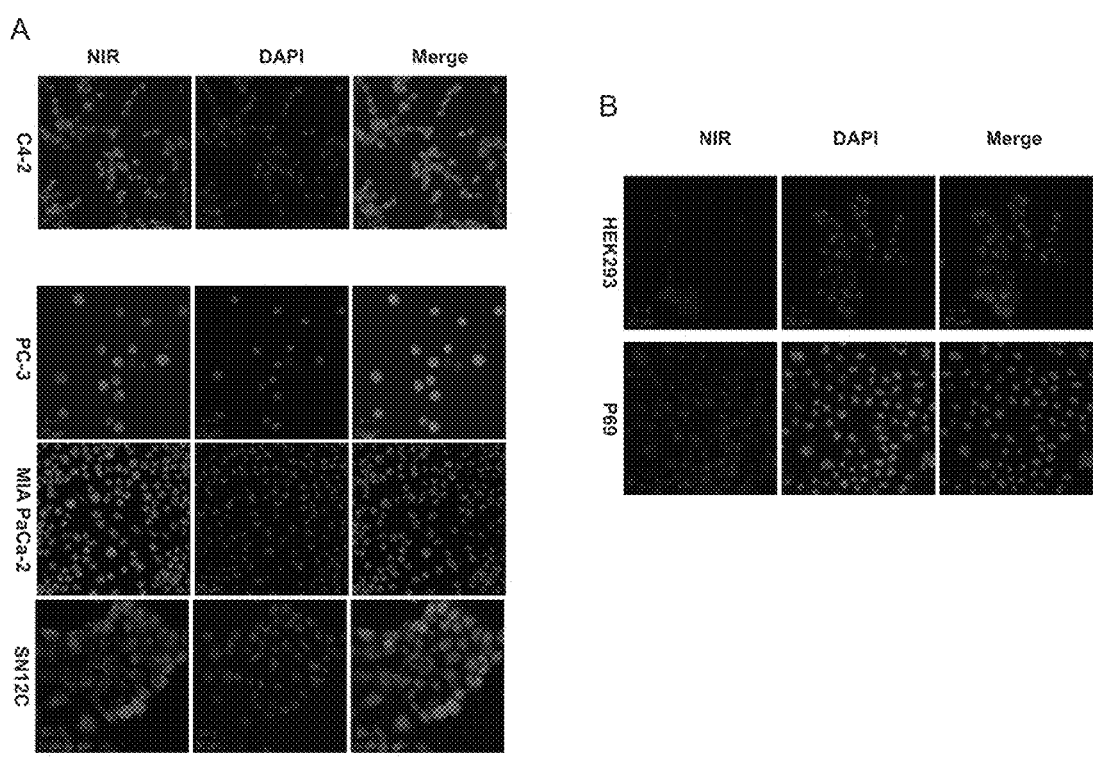
Figures 9 A-B

PC-3 (WT and MAOA-overexpressing)

ARCaP$_M$ (scramble and MAOA-KD)

SEQUENCE LISTING

<160> NUMBER OF SEQ ID NOS: 11

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
ccggcggata ttctctgtca ccaatctcga gattggtgac agagaatatc cgttttg        58

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
gtgtcagcca aagcatggag a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
cagtcaagag tttggcagca g                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
cagccacccg agattgagca                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tagtagcgac gggcggtgtg                                                20

<210> SEQ ID NO 6
<211> LENGTH: 10
<212> TYPE: DNA
<213> ORGANISM: Artificial Sequence
<220> FEATURE:
<223> OTHER INFORMATION: Canonical Fox01-binding site

<400> SEQUENCE: 6
cgataaacaa                                                           10

<210> SEQ ID NO 7
<211> LENGTH: 27
<212> TYPE: DNA
<213> ORGANISM: Homo sapiens

<400> SEQUENCE: 7
actgctgccc ccaaactttc cgcctgc                                        27

<210> SEQ ID NO 8
<211> LENGTH: 27
<212> TYPE: DNA
<213> ORGANISM: Pan troglodytes

<400> SEQUENCE: 8
aaaatataga ccaaactcta aggttct                                        27

<210> SEQ ID NO 9
<211> LENGTH: 27
<212> TYPE: DNA
<213> ORGANISM: Mus musculus

<400> SEQUENCE: 9

```
accgctgccc ccaaactttc cgcccgc                                          27
```

<210> SEQ ID NO 10
<211> LENGTH: 27
<212> TYPE: DNA
<213> ORGANISM: Rattus norvegicus

<400> SEQUENCE: 10

```
actgctgccc ccaaactttc cgcccgc                                          27
```

<210> SEQ ID NO 11
<211> LENGTH: 27
<212> TYPE: DNA
<213> ORGANISM: Bos taurus

<400> SEQUENCE: 11

```
actgctgccc ccaaactttc cgcttgc                                          27
```

MONOAMINE OXIDASE INHIBITORS AND METHODS FOR TREATMENT AND DIAGNOSIS OF PROSTATE CANCER

CROSS-REFERENCE TO RELATED APPLICATIONS

This application claims an invention which was disclosed in Provisional Application No. 61/511,920 filed Jul. 26, 2011, the entire content of which is hereby incorporated herein by reference.

STATEMENT REGARDING FEDERALLY SPONSORED RESEARCH AND DEVELOPMENT

This invention was made with government support under Contract Nos. P01-CA98912, DAMD-17-03-02-0033, R01-CA122602, R01-MH39085 awarded by the National Institute of Health. The government has certain rights in the invention.

FIELD OF THE INVENTION

The present invention relates generally to inhibition of monoamine oxidases (MAOs) and their inhibitors (MAOIs) as strategies to treat cancer, particularly prostate cancer. This invention also relates to imaging, screening, diagnostics, and therapeutic methods of cancer. In addition, this invention further relates to cancer biomarkers and methods for differentiating indolent from virulent prostate cancer.

BACKGROUND OF THE INVENTION

Prostate cancer is the third most common cause of death from cancer in men of all ages and is the most common cause of death from cancer in men over age of 75. Current treatments for prostate cancer include (1) hormonal therapy, (2) chemotherapy, (3) radiation therapy, and (4) surgery. However, they are only effective for patients during the early stages of the disease. There are also undesired side effects associated with each of these treatment modalities. Moreover, for patients with advanced stages of castration-resistant and metastatic prostate cancers, these treatments are only partially effective.

Supplemental or combination therapies may improve the outcome in advanced patients. For instance, patients subjected to androgen ablation therapy with either chemical castration with a LH-RH agonist or surgical castration have benefited by the combination with an antiandrogen like bicalutamide. Patients who failed these hormonal therapies are often benefited by selective chemotherapy such as docetaxel and denosumab and additional hormonal therapy to deplete residual endogenous androgen synthesis (e.g. a CYP17 inhibitor, abiraterone). Despite the improvement, these additional therapies, in general, are only capable of prolonged survival by a few months.

Prognosis and staging of prostate cancer are typically evaluated using the Gleason grading system. A Gleason score is given to prostate cancer based on its microscopic appearance. Cancers with a higher Gleason score are more aggressive and have a worse prognosis. A Gleason score is determined by a pathologist who visually inspects a biopsy sample and then assigning a score to the observed tumor pattern. However, the Gleason system is entirely reliant upon human visual examination, which is prone to error with significant limitations on early detection.

In view of the above, there is an urgent, unmet need for more effective mechanism-based therapies and noninvasive early-stage diagnostic techniques to differentiate indolent from virulent forms of prostate cancer so that overtreatment of this disease can be avoided.

SUMMARY OF THE INVENTION

Briefly, the present invention is based, in part, on the surprising discovery that monoamine oxidases exhibit differential expressions/activities in cancerous cells and that inhibitors of monoamine oxidases (MAOs) are capable of repressing the growth of cancer cells in vitro and tumor xenografts in vivo.

MAOs are a family of enzymes that catalyze the oxidation of monamines. They are bound to the outer membrane of mitochondria in most cell types in the body. In humans, there are two isoforms of MAO, MAO-A and MAO-B. The two forms of MAOs are a crucial pair of oxidative enzymes that deaminate biogenic and dietary amines, including monoamine neurotransmitters, resulting in the production of hydrogen peroxide ($H_2O_2$). Both isoforms of MAO play key roles and have diverse functions in normal physiology and disease states, such as modulating emotions and behaviors. Because of the vital role that MAOs play in the inactivation of neurotransmitters, MAO dysfunction (too much or too little MAO activity) is thought to be responsible for a number of psychiatric and neurological disorders. For example, unusually high or low levels of MAOs in the body have been associated with depression, schizophrenia, substance abuse, attention deficit disorder, migraines, and irregular sexual maturation. Therefore, MAO was previously known as a target for psychiatric and neurological disorders.

In the present invention, it was unexpectedly discovered that increase of MAO-A activity or expression is correlated with the progression of human prostate cancer. For example, it has been demonstrated that clorgyline, a potent MAO-A inhibitor, is capable of repressing the growth of human prostate cancer cells in vitro and tumor xenografts in vivo. This finding establishes MAOs as a target for cancer.

Accordingly, a first aspect of the present invention is directed to a novel MAO inhibitor selected from the group consisting of compounds 11-14 as shown below:

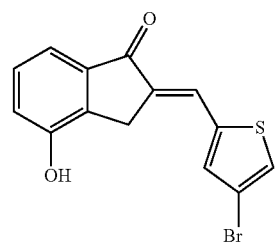

11

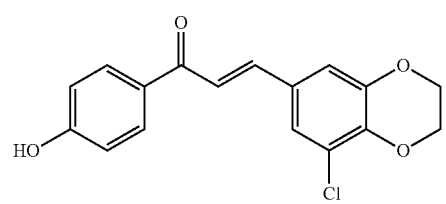

12

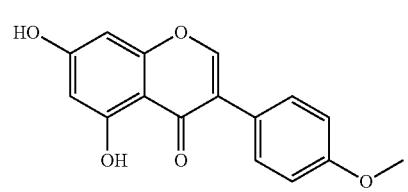

13

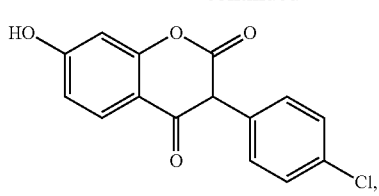

14 and a salt thereof. These compounds are commercially available compounds with newly discovered MAO inhibitory activities. They may be purchased from commercial sources, including but not limited to, Aurora Screening Library, Enamine HTS Collection and/or Interchim Screening Library. Thus, this aspect of the invention provides compositions comprising useful for inhibiting MAO activity, comprising one or more compounds selected from the group consisting of compounds 11-14. This aspect of the invention also provides a method for inhibiting MAO activity by contacting a cell with one or more MAO inhibitors selected from the group consisting of compounds 11-14.

In addition to the above disclosed inhibitors, the present invention has also unexpectedly discovered that nanoparticles that are preferential uptaken by cancer cells (e.g. near infrared dies) may be used as a delivery vehicle to deliver a pharmaceutically active agent (e.g. a cytotoxic compound) to cancer cells. For example, the present invention has succeeded in conjugating near-infrared dye nanoparticles such as IR-783 to an active agent such as a MAO inhibitor described above and demonstrated that the resulting nanoconjugates remain preferentially uptaken by cancer cells.

Hence, a second aspect of the present invention is directed to a nano-conjugate capable of preferentially or selectively targeting cancer cells. Nano-conjugates in accordance with this aspect of the invention will generally have an NIR dye nanoparticle conjugated to a cytotoxic compound. Exemplary NIR dyes may include conjugated polyene functional groups, such as one found in IR-783, IR-780, IR-786, and MHI-148 but are not limited thereto. Exemplary cytotoxic compound may include MAO inhibitors, docetaxel, cisplatin, carboplatin, oxaliplatin, doxorubicin, temozolomide, gemcitabine, anthramycin, camptothecin, topotecan, lonidamine, mitomycin, imexon, dacarbazide, PK-11195, but are not limited thereto. Conjugation of the NIR dye nanoparticle to the cytotoxic compound may be achieved by any suitable chemical means known in the art.

In one preferred embodiment, exemplary nano-conjugates of the present invention will generally have at least two functional groups with a cytotoxic element (e.g. an MAO inhibitor) attached to a light emissive element (e.g. NIR dye nanoparticle) via a linker containing at least one C and two H atoms. Preferably, at least two unsaturated structures containing one unsaturated double or triple bond are linked via a backbone chain of 1-3, 1-5, or 1-15 atoms to one heterocycle.

An exemplary linker is one having the following general formula:

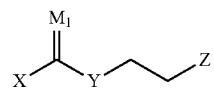

wherein $M_1$ is O or S; and wherein at least two of X, Y, and Z participate in bonds to unsaturated and/or aromatic groups A and B (not shown) which proceed through additional carbon, oxygen or nitrogen atoms. Any of X, Y, and Z not participating in a bond to group A or B is substituted with hydrogen or lower aliphatic group, such as $C_1$-$C_6$ alkyl.

As used herein, the term "backbone chain" refers to the chain of atoms linking the two unsaturated structures together, not taking into account said chain.

For example, a conjugate or nanoparticle-encapsulated conjugate (herein referred to as nano-conjugate) in accordance with embodiments of the invention may be one having the following formula:

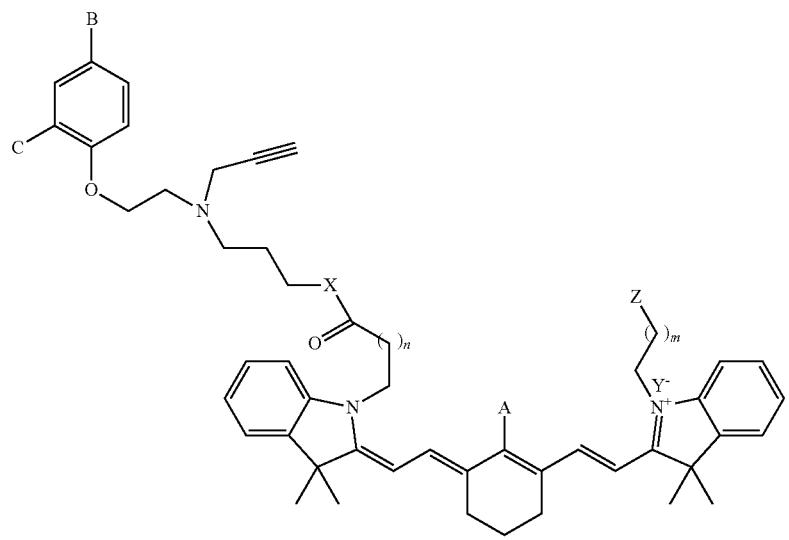

A, B, or C = F, Cl, Br, I
X = NH, O, S
Y = Cl, Br, I, mesyl, tosyl
m, n = 1-15

In another embodiment, X and Y are as above and Z is selected from the group consisting of

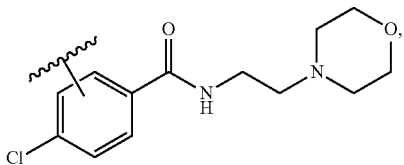

wherein the covalent link is attached to the aromatic ring. This compound is herein referred to as MHI-moclobemide, a MAO-A specific reversible inhibitor.

In another embodiment, X and Y are same as above, and Z is

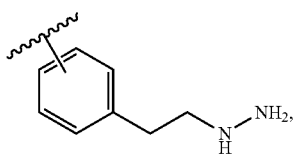

wherein the covalent bond is also attached to the aromatic ring. This compound is herein referred to as MHI-phenelzine, a MAO-A and -B inhibitor.

In still another embodiment, X and Y are same as above, and Z is (±)-trans-2-phenylcyclopropan-1-amine having the formula:

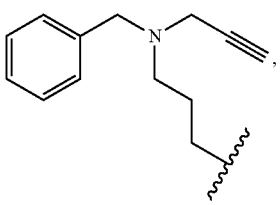 [SMILES: *CCCN(CC#C)Cc1ccccc1]

wherein covalent attachment is through the aromatic ring.

This compound is herein referred to as MHI-tranylcypromine, which is a MAO-A and -B inhibitor.

In still another embodiment, X and Y are same as above, and Z is N-Benzyl-N-methylprop-2-yn-1-amine, having the following formula:

wherein covalent linkage is attached to the nitrogen as indicated by the curly line. This compound is herein referred to as MHI-pargyline, a MAO-A and -B inhibitor with a preference for MAO-B.

In a preferred embodiment, Y is S; X is a group having the following formula:

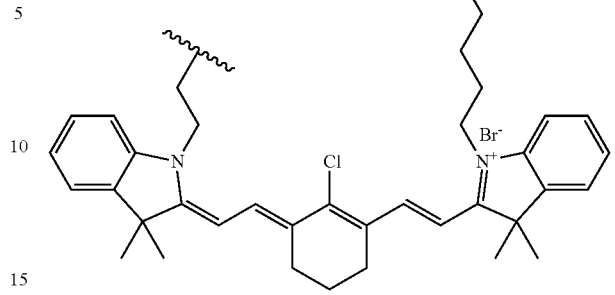

and Z is a group having the following formula:

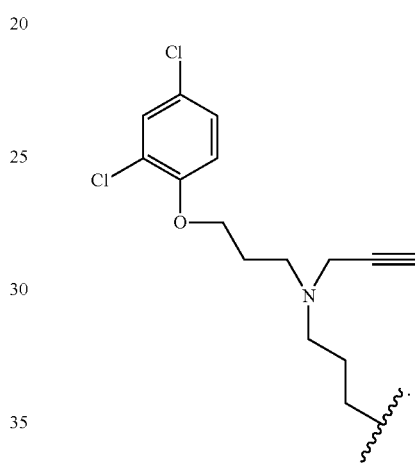

This compound is referred to herein as MHI-clorgyline, which is a MAO-A specific irreversible inhibitor.

In yet another embodiment, X and Y are same as above, Z is one selected from the following:

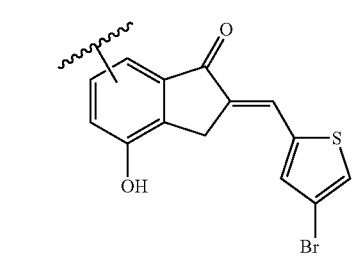

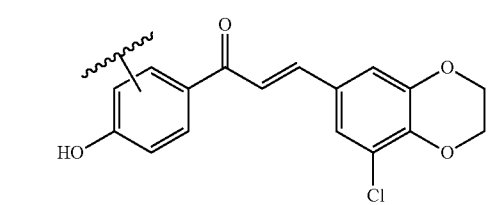

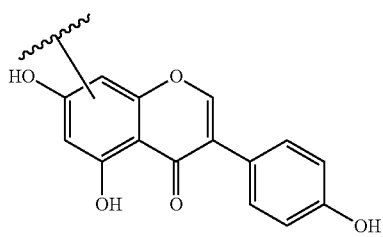

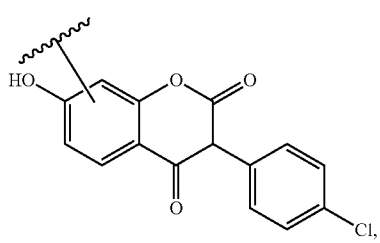

wherein covalent linkage is attached to the aromatic rings. This group of compounds is collectively referred to herein as MHI-MAOIs.

The MHI-MAOIs can be conveniently prepared in two steps from MHI-148 and inhibitor through reduction of MHI-148 with lithium aluminum hydride or diborane and subsequent conjugation of the resulting diol with the MAOI by, for example, but without being limited to, Mitsunobu reaction, to give conjugate 11D.

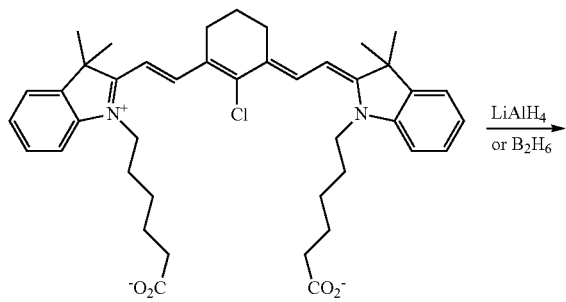

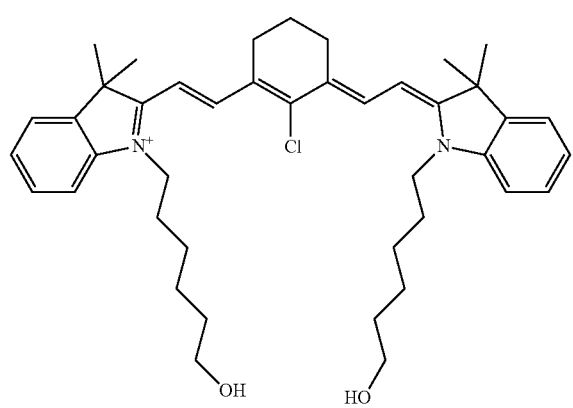

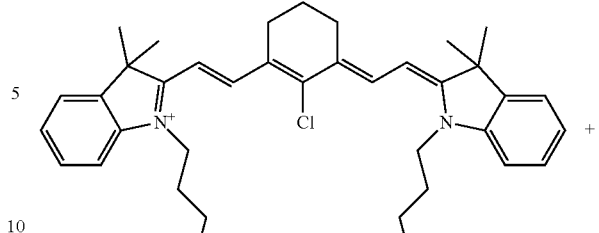

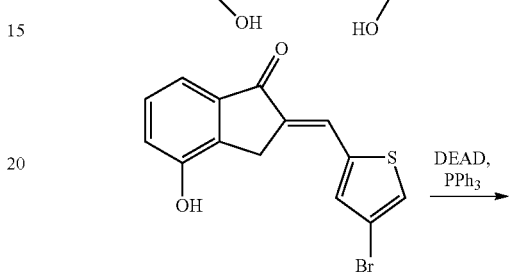

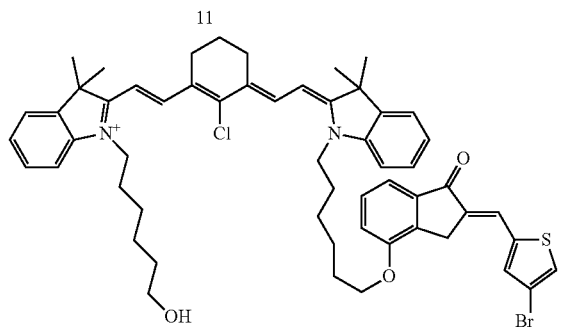

MHI-11D

In still another embodiment, Y and Z are same as above, X is one having the following formula:

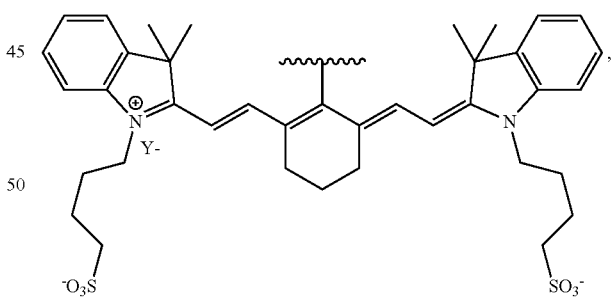

wherein the covalent linkage is attached to the cyclohexene ring of the molecule. This group of compounds is collectively referred to herein as NIR-MAOIs.

A third aspect of the present invention is directed to a method for forming an NIR dye-based nano-conjugate capable of preferentially targeting cancerous cells. Methods in accordance with this aspect of the invention will generally include the steps of chemically conjugating an NIR dye nanoparticle to a cytotoxic compound. Suitable NIR dyes and cytotoxic compounds are as described above.

A forth aspect of the present invention is directed to a pharmaceutical composition useful for treating cancer, and methods of treating cancer using the compositions. Compositions in accordance with this aspect of the invention will generally include an active agent capable of inhibiting MAO activity; and a physiologically suitable carrier. In some preferred embodiments, the active agent is a MAO inhibitor known in the art. Exemplary MAO inhibitor may include, but not limited to moclobemide, phenelzine, tranylcypromine, pargyline, and clorgyline. Nucleic acids capable of inhibiting, down-regulating or silencing the expression of MAO may also be advantageously used. Exemplary nucleic acid MAO inhibitors may include siRNA, shRNA, antisense, or any other type of nucleic acid-based gene silencing agents commonly known in the art, such as decoys, ribozymes, and aptamers. Such preferred embodiments can be used, either alone or in combination with the described herein pharmaceutical compositions as cancer therapeutics.

In one exemplary embodiment, gene silencing or knockdown of MAO-A in human prostate cancer cells with shRNA can be exemplified as follows: in a 48-well tissue culture plate, $6 \times 10^4$ human prostate cancer cells per well in 250 ul normal culture medium were seeded 24 hrs prior to viral infection, and the cells should be approximately 50% confluent on the day of infection. A mixture of 40 ul of human shMAOA lentiviral transduction particles ($5 \times 10^6$ titer/ml) with polybrene (at a final concentration of 5 ug/ml) in 100 ul medium (without FBS and anti-biotics) was prepared and added into cells for a subsequent incubation for 4 hrs to overnight. The culture medium was replenished after 4 hrs to overnight. Cells were then treated with 2-10 ng/ml puromycin 48 hrs after infection for selection consecutively for 2 weeks, and the medium supplemented with puromycin was replenished every 3-4 days. Stable MAOA-KD cells were validated by Western blot and real-time RT-PCR examination of MAOA gene expression, and were maintained in the culture medium supplemented with puromycin at the same concentrations for selection. The shRNA sequence against human MAOA cDNA is: CCGGCGGAT-ATTCTCTGTCACCAATCTCGAGATTGGTGACAGA-GAATATCCGTTTTTG (SEQ ID NO:1), as adapted from a Sigma-Aldrich product (catalog# NM_000240_TRCN0000046009).

In other preferred embodiments, the active agent is an NIR dye-based conjugate as described above. In still other preferred embodiments, the active agent is one selected from compounds 11-14 that are available from commercial sources, including but not limited to, Aurora Screening Library, Enamine HTS Collection and/or Interchim Screening Library.

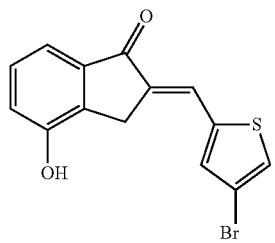

11

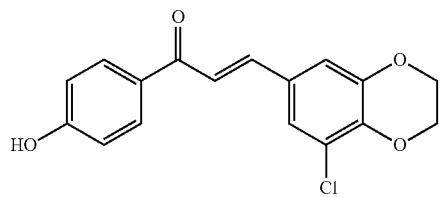

12

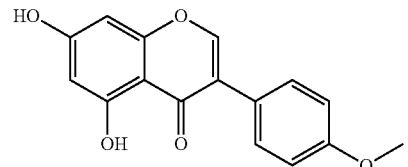

13

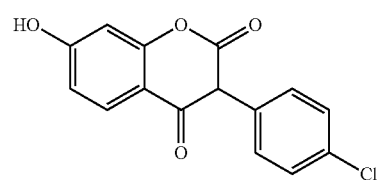

14

A fifth aspect of the present invention is directed to a method of delivering a pharmaceutical agent to a cancer cell. Methods in accordance with this aspect of the invention will generally include the steps of conjugating the pharmaceutical agent to an NIR dye; and contacting the conjugate with the cancer cell. In some preferred embodiments, the pharmaceutical agent is a cytotoxic agent. Exemplary cytotoxic agent may include an alkylating agent, an inhibitor of microtubule formation, and an aromatase inhibitor, but are not limited thereto.

A sixth aspect of the present invention is directed to a method of inhibiting MAO activity in a cancer cell. Methods in accordance with this aspect of the invention will generally include the steps of contacting a cell with an inhibitory agent, wherein said inhibitory agent is selected from the group consisting of a MAO inhibitor, a nano-conjugate with a NIR dye conjugated to a MAO inhibitor, and a combination thereof. Any MAO inhibitor known in the art or herein disclosed, both pharmacological and nucleic-acid based, may be advantageously used.

Where prostate cancer is concerned, it is a further discovery of the present invention that MAO-A is associated with chemo and radiation resistance in human prostate cancer whereas MAO-B has a unique expression pattern in human prostate cancer-associated stromal cells. As mentioned above, MAOs are mitochondrial-bound enzymes that catalyze the degradation of monoamine neurotransmitters and dietary amines via oxidative deamination. They are encoded by their genes located in the X chromosome [1, 2]. The by-product of MAO catalysis is hydrogen peroxide, a major source of reactive oxygen species (ROS), which can predispose cancer cells to DNA damage and promote tumor initiation and progression [3]. Modulation of intracellular ROS levels in prostate cancer cells could affect the sensitivity of prostate cancer cells toward hormonal, chemo- and radiation therapy [4]. Moreover, MAOs are responsible for the generation of ROS, in the presence of their biogenic amine substrates from the diet or physiological sources in an epithelial versus stromal cellular compartments. In addition, since prostate stroma is known to drive the progression of prostate cancer, by differentiating the forms, the amount, and the physical location of MAOs in prostate cancer tissue specimens, indolent forms of human prostate cancer may be differentiated from virulent forms. In short, it is an unexpected discovery of the present invention that MAOs are capable of serving as biomarkers for screening, diagnosing, and differentiating prostate cancer forms in patients. Based on the observation that MAO-A and MAO-B differs in their localization, a treatment strategy targeting both MAO-A in prostate cancer epithelium and MAO-B in prostate cancer-associated stroma is also devised.

Accordingly, a seventh aspect of the present invention is directed to a method of differentiating different forms of prostate cancer, comprising assaying MAO activity and location patterns in prostate tissues; and determining a cancer form characterization according to said MAO activity and location patterns. The said MAO activity can be determined, for example, by real-time PCR that measures the MAO-A expression in prostate biopsy as described below:

The biopsy samples should be homogenized in Trizol, and RNA isolated. Next, 1 ug of total RNA will be reverse transcribed in 25 ul volume, then 2 ul of the sample (cDNA) is diluted 1/10 into 20 ul, 5 ul of this sample will be used as template for MAO A measurement. Another 2 ul will be diluted 1/50 into 100 ul, 5 ul of this sample is used for ribosomal RNA control template, The primer sequence for human MAO A specific primer can be as folows :

```
                                          (SEQ ID NO: 2)
MAO A E1F168 GTG TCA GCC AAA GCA TGG AGA 188

(SEQ ID NO: 3)
MAO A E2R281 CAG TCA AGA GTT TGG CAG CAG 261
113 bp PCR product
```

The primer sequence for 18 s ribosomal RNA are as follows:

```
                                          (SEQ ID NO: 4)
    F1565 CAG CCA CCC GAG ATT GAG CA (SEQ ID NO: 5)
    R1816 TAG TAG CGA CGG GCG GTG TG
    253 bp PCR product
```

PCR condition: 95 degrees C.×4 min 1 cycle
95 degree×30 sec
60 degree×30 sec
72 degree×30 sec 40 cycles.

Those skilled in the art will recognize that the above example is for illustration only and other currently known or future invented methods of measurement may also be used to determine MAO activity.

An eighth aspect of the present invention is directed to a method of screening a patient for risk of cancer, comprising assaying MAO activity in the patient; comparing said activity to a reference; and determining a risk level based on the comparison. The said MAO activity can be determined, for example, by real-time PCR that measures the MAO-A expression in prostate biopsy as described below:

The biopsy samples should be homogenized in Trizol, and RNA isolated. Next, 1 ug of total RNA will be reverse transcribed in 25 ul volume, then 2 ul of the sample (cDNA) is diluted 1/10 into 20 ul, 5 ul of this sample will be used as template for MAO A measurement. Another 2 ul will be diluted 1/50 into 100 ul, 5 ul of this sample is used for ribosomal RNA control template.

The primer sequence for human MAO A specific primer can be as folows :

```
                                          (SEQ ID NO: 2)
MAO A E1F168 GTG TCA GCC AAA GCA TGG AGA 188

(SEQ ID NO: 3)
MAO A E2R281 CAG TCA AGA GTT TGG CAG CAG 261
113 bp PCR product
```

The primer sequence for 18 s ribosomal RNA are as follows:

```
                                          (SEQ ID NO: 4)
    F1565 CAG CCA CCC GAG ATT GAG CA (SEQ ID NO: 5)
    R1816 TAG TAG CGA CGG GCG GTG TG
    253 bp PCR product
```

PCR condition: 95 degrees C.×4 min 1 cycle
95 degree×30 sec
60 degree×30 sec
72 degree×30 sec 40 cycles.

Those skilled in the art will also recognize that the above example is for illustration only and other currently known or future invented methods of measurement may also be used to determine MAO activity.

A ninth aspect of the present invention is directed to a method of treating cancer. Methods in accordance with this aspect of the invention will generally include the steps of administering to a subject a pharmaceutical agent capable of inhibiting MAOs in cancer cells. The type of cancers that may be treated by methods in accordance with this aspect of the invention may include prostate, brain, colon, aggressive fibromatosis, but not limited thereto. The pharmaceutical agent may be any of the above described compositions, nano-conjugates, or inhibitors. In a preferred embodiment, the cancer is prostate cancer. In a further preferred embodiment, treatment of prostate cancer may include administering a first pharmaceutically active agent targeting MAO-A in epithelium with clorgyline and a second pharmaceutically active agent targeting MAO-B in stroma with deprenyl. Said first and second pharmaceutically active agent may be different agent or the same agent, so long as they are effective in inhibiting the respective MAO isoform in the respective tissue type.

An tenth aspect of the present invention is directed to a method of monitoring treatment progress in a cancer patient being treated with a pharmaceutical composition comprising a NIR dye-based nano-conjugate. Methods in accordance with this aspect of the invention will generally include the steps of obtaining successive NIR image of the patient; and comparing said successive NIR images to determine progression of said treatment. The effect of conjugate on prostate tumor growth and metastasis can be determined by imaging and IHC analysis. The said imaging can be done, for example, with Xenogen IVIS 200 instrument. This system allows researchers to use real-time, non-invasive imaging to monitor and record cellullar and genetic activity in vivo. Integrated into the system are both a bioluminescence system and a fluorescence system and the capability to easily switch between modalities. A laser scanner also provides 3D surface topography for single-view diffuse tomographic reconstructions of internal sources. Background noise is minimized while sensitivity is maximized using a 26 mm square CCD which is cryogenically cooled. Scans generally take 1-10 minutes to complete with five field of view options ranging from 4 cms to 25 cms.

An eleventh aspect of the present invention is directed to a method of modulating ROS levels in cells. Methods in accordance with this aspect of the invention will generally include the steps of contacting a cell with a MAO inhibitory agent. Suitable MAO inhibitory agent may be any of the MAO inhibitors, nano-conjugates, or pharmaceutical compositions described above. These agents can be used either alone or in combination with mitochondria-directed antioxidants, such as lipoic acid, N-acetyl-L-carnitine and N-Acetyl-L-cysteine.

Other aspects and advantages of the present invention will become apparent from the following detailed description and the appended claims.

BRIEF DESCRIPTION OF THE DRAWINGS

"The file of this patent contains at least one drawing executed in color. Copies of this patent with color drawings will be provided by the Office upon request and payment of the necessary fee".

FIG. 9A-9E shows that IR-783-docetaxel was found to be uptaken into human prostate cancer cells (C4-2, PC-3), pancreatic cancer cells (MIA-PaCa2) and renal cancer cells (SN12C, see panel a); this NIR-docetaxel conjugate was found not uptaken into human normal prostate epithelial cells (P69) and a fetal human kidney 293 cells (see panel b). Cytotoxicity assays shows that this NIR-docetaxel conjugate exerted growth inhibitory effects on a panel of human cancer cell lines in vitro in a concentration dependent manner (see panel c). Using human renal cancer (SN12C) and normal fetal kidney cells (HFK293) as models, we observed that this dye-drug conjugate has equal effectiveness like the parental drug, docetaxel, in killing SN12C but not HFK293 cells, a result consistent with the suggestion that the dye-drug conjugate entered cancer but not normal cells.

DETAILED DESCRIPTION

Definition

Unless otherwise indicated herein, all terms used herein have the meanings that the Willis would have to those skilled in the art of the present invention. Practitioners are particularly directed to current textbooks for definitions and terms of the art. It is to be understood, however, that this invention is not limited to the particular methodology, protocols, and reagents described, as these may vary.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

A "therapeutically effective amount" of a monoamine inhibitor is an amount sufficient to carry out a specifically stated purpose. An "effective amount" may be determined empirically and in a routine manner in relation to the stated purpose.

A "Carrier" or "Carriers" as used herein include pharmaceutically acceptable carriers, excipients, or stabilizers which are nontoxic to the cell or mammal being exposed thereto at the dosages and concentrations employed. The physiologically acceptable carrier may be a sterile aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

Recent studies indicate that increased MAO-A is associated with prostate cancer progression [5]; conversely, pharmacological MAO-A inhibition or lentiviral shRNA-mediated silencing of MAO-A significantly reduced the growth of prostate cancer cells in vitro and tumor xenograft in vivo [6-8]. Furthermore, our data showed that MAO-A induced epithelial-to-mesenchymal transition (EMT) in human prostate cancer cells, by promoting the loss of E-cadherin (an epithelial marker) expression, up-regulation of vimentin (a mesenchymal marker) levels as well as increased invasion and migration of prostate cancer cells. These results suggest that MAO-A expression may be correlated with the metastatic potential of prostate cancer cells. Taken together, this evidence strongly supports the role of MAO-A as a potential novel target for the treatment of human prostate cancer.

Figures 1A, 1B:
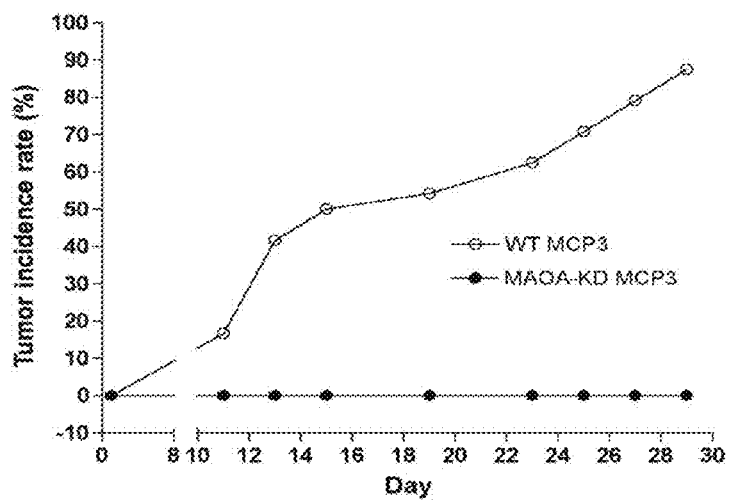
FIG. 1A-B shows the tumor xenografts growth rates were much reduced in mice injected with MCP3 cells (a mouse cell lines with PTEN and p53 double KO, see filled circles) with MAO-A knock down compared with WT MCP3 cells (open circles). There was no tumor growth when MAO-A knock down MCP3 prostate cancer cells ($1 \times 10^6$ cells) were injected in mice, whereas significant number of tumors were found in WT MCP3 cell injected mice.
Figure 1C:
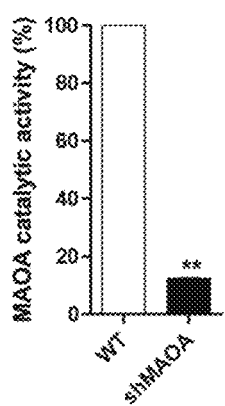
FIG. 1C shows that MAO-A expression is correlated with cell proliferation profiles in human and murine cancer cells. $2 \times 10^4$ human or murine prostate cancer cells of manipulated MAO-A expression were seeded, and cell numbers were counted consecutively over a 6-day period. Experiments were performed in triplicate. shMAO-A, MAO-A knockdown by shRNA lentiviral infection.

We have found that monoamine oxidase A (MAO-A) knock-down (KD) prostate cancer cells did not grow when injected into mice. This result was dramatically different from the WT prostate cancer cells (See FIG. 1). A total of 10 wild-type (WT) mice in C57BL/6 background were used. Six mice were injected with WT MCP3 (PTEN/p53 double knockout) prostate carcinoma cells of C57 mouse strain origin, 4 sites per mouse with a total of 24 sites. Four mice were injected with MAO-A knock-down (KD) MCP3 cells, 4 sites per mouse with a total 16 sites. The number of tumors was counted on the days as indicated. The tumor incidence rate is defined as the total number of detectable tumors divided by the total number of the sites injected. As shown in FIG. 1, the tumor growth rate in mouse tumor xenografts injected with MAO-A knock down MCP3 cells (filled circles) compared with WT MCP3 cells (open circles). There was no tumor growth when MAO-A knock down MCP3 (PTEN and p53 double KO) prostate cancer cells ($1 \times 10^6$ cells) were injected in mice, whereas significant number of tumors were found in WT MCP3 cell injected mice.

Figure 10:
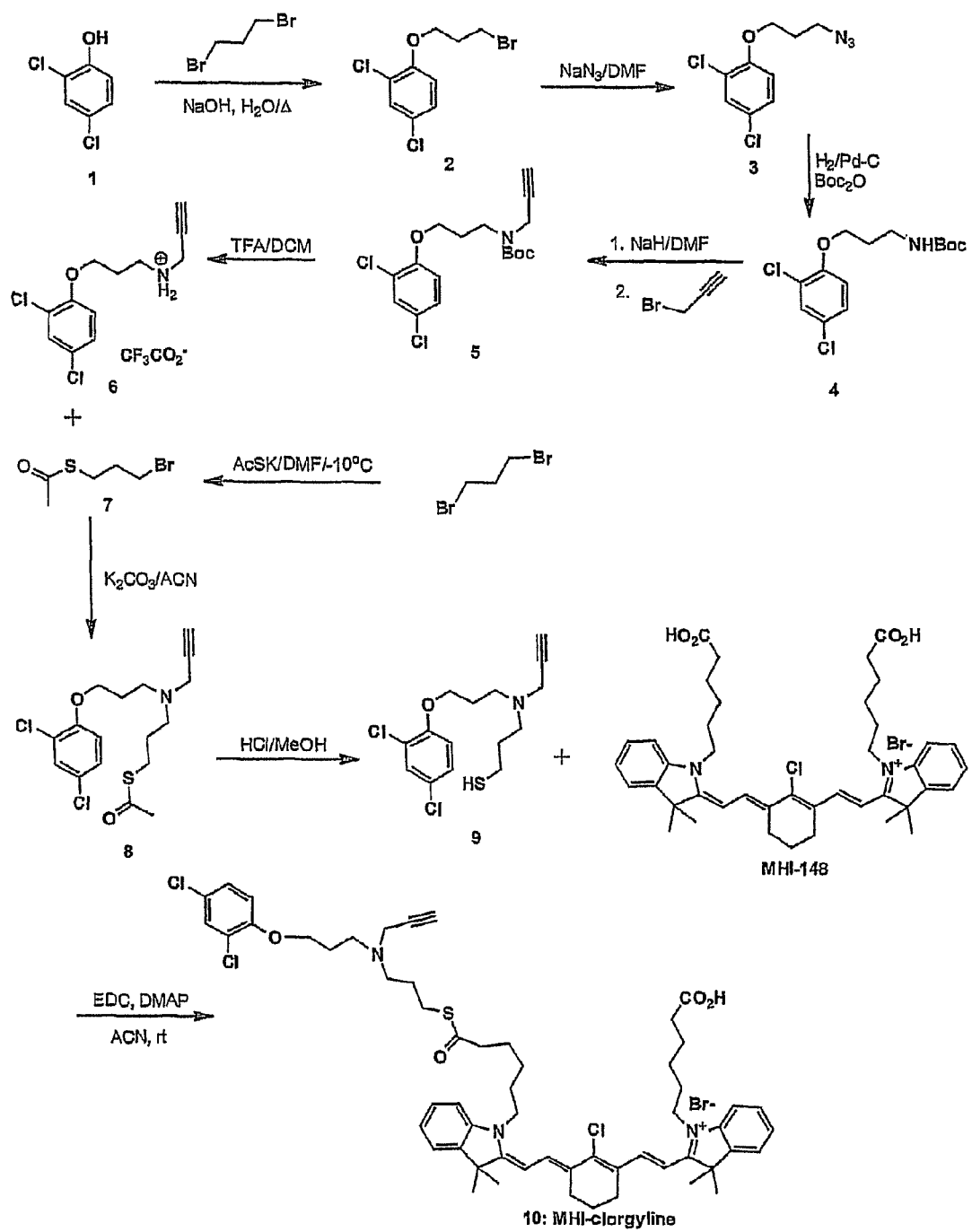
FIG. 10 shows an exemplary synthetic route leading to MHI-clorgyline.
Figure 11:
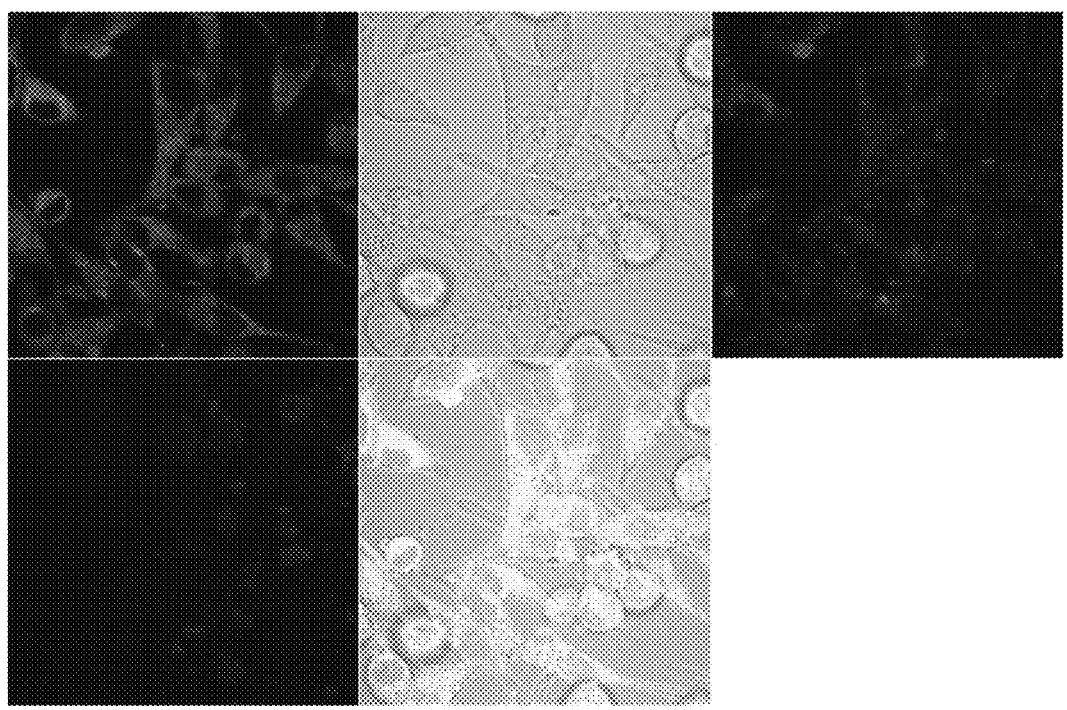
FIG. 11 shows exemplary confocal images of C4-2B prostate cancer cells treated with Mitotracker Green (top left), compound 10 (top right), DAPI (bottom left) and overlay (bottom center. The brightfield image is in the top center.
Figure 12:
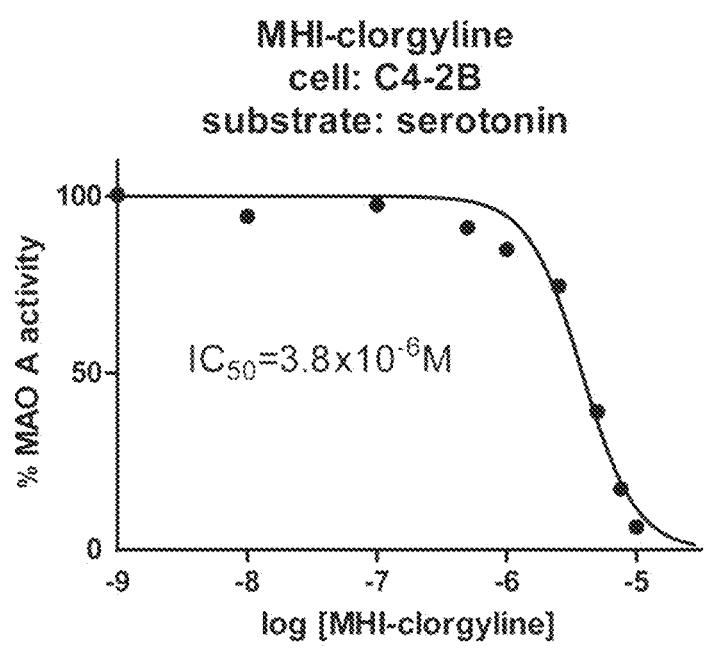
FIG. 12 shows an exemplary MAO-A inhibition curve for MHI-clorgyline 10. Compound 10 was pre-incubated with $1 \times 10^6$ prostate C4-2B cells at 37° C. for 20 min. Then, MAO A substrate C-14 serotonin was added to the incubation solution for 37° C. 20 min. At the end of the incubation, the reaction product was extracted and the radioactivity was counted. The MAO-A activity was expressed as 69.6 nM product formed/20 min/mg protein. The activity without the presence of inhibitor, compound 10, was taken as 100%.

One aspect of the present invention is a method in which a MAO-A inhibitor, clorgyline, can be delivered to cancer cells and tissues by chemically conjugating clorgyline to a NIR dye. The NIR-dye-clorgyline conjugate is expected to be uptaken by cancer but not normal cells thus avoiding systemic toxicity of this MAOI. Laser-scanning confocal microscopy can be used to determine cellular uptake and localization of the nano-clorgyline within cells (LNCaP, C4-2, and ARCaP$_M$ prostate cancer cell lines). This class of NIR dyes can be readily uptake into cancer cells via organic anion transporting peptides. FIGS. 10 and 11 show that NIR dye (IR-783) conjugate of docetaxel, IR-783-docetaxel, was found to be uptaken into human prostate cancer cells, pancreatic cancer cells and renal cancer cells but not human prostate epithelial cells or fetal human kidney cells, suggesting such NIR dye-chemotherapeutic agent conjugates enter cancer cells but not normal cells.

To determine the ability of nano-clorgyline to inhibit activity of MAO-A. MAO-A inhibition curve is obtained for prostate cancer cells LNCaP, C4-2, and ARCaP$_M$ cell lines and compared with that clorgyline itself. These cell lines have moderate to high MAO-A activity. IC$_{50}$ of nano-clorgyline is determined and compared to that of clorgyline.

To study the effect of nano-clorgyline and NIR dyes (IR-783, IR-780 and MHI-148)-clorgyline on MAO-A and MAO-B inhibition. MAO-A and MAO-B inhibition curves is performed in mice. ICs$_{50}$ are determined.

To study the localization of nano-clorgyline, and NIR dyes-clorgyline conjugates and its effect on tumor growth, prostate cells are injected into mice. In one exemplary experiment, mice are divided into 3 groups separately injected with (a) nano-clorgyline of NIR dyes-clorgyline, (b) clorgyline itself, and (3) dye only, respectively. The location of the nano-clorgyline was imaged, the tumor's growth (size, number, and weight) was monitored, and the results from the 3 groups were compared.

The result of the experiment demonstrated the effect of nano-clorgyline on tumor growth. Having established the effectiveness of the clorgyline nano-conjugate, it will be appreciated by those skilled in the art that other parameters such as the concentration required for inhibition of MAO-A activity and tumor growth may be readily determined via routine experimentation.

The MAO-A inhibitors, including the NIR dyes-MAOI conjugates thereof, may be used alone or in combination with the existing treatments on tumor growth and metastasis such as (a) surgical castration; (b) radiation (c) docetaxel; (d) abiraterone.

Furthermore, this clorgyline-dye conjugate may be used in connection with methods for treatment of prostate cancer and methods for diagnosis and monitoring of the progression of the prostate cancers by administering to a patient a composition comprising an effective amount of the clorgyline-dye conjugate.

Design, Synthesis, Encapsulation and Testing of Clorgyline-dye Conjugate Nanoparticles (Nano-clorgyline) in Cells.

1. IR-783 Nanoparticle Dye Conjugate

Figure 2:
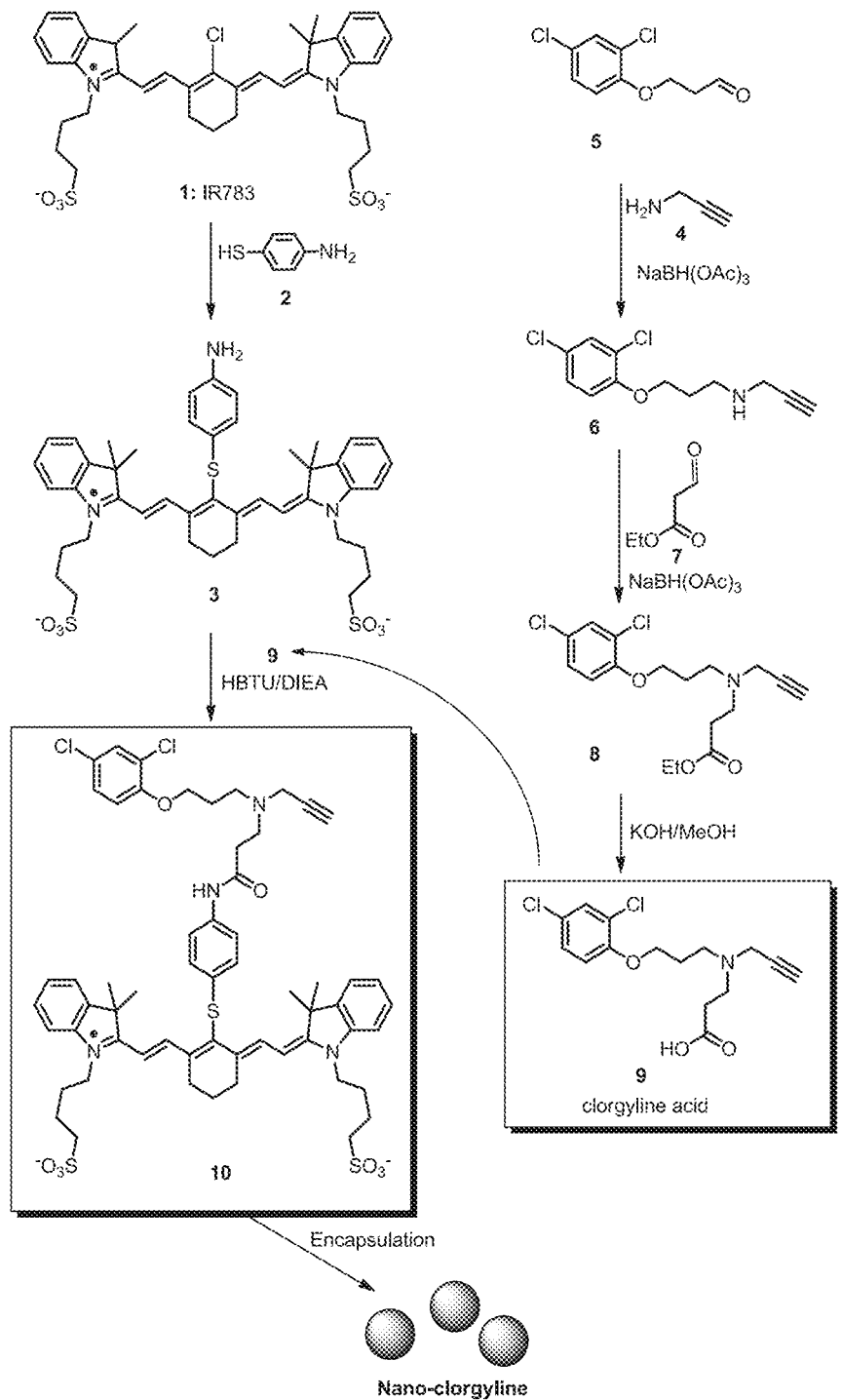
FIG. 2 shows the synthetic scheme for clorgyline-NIR dye conjugate and preparation of nano-clorgyline.
Figure 3:
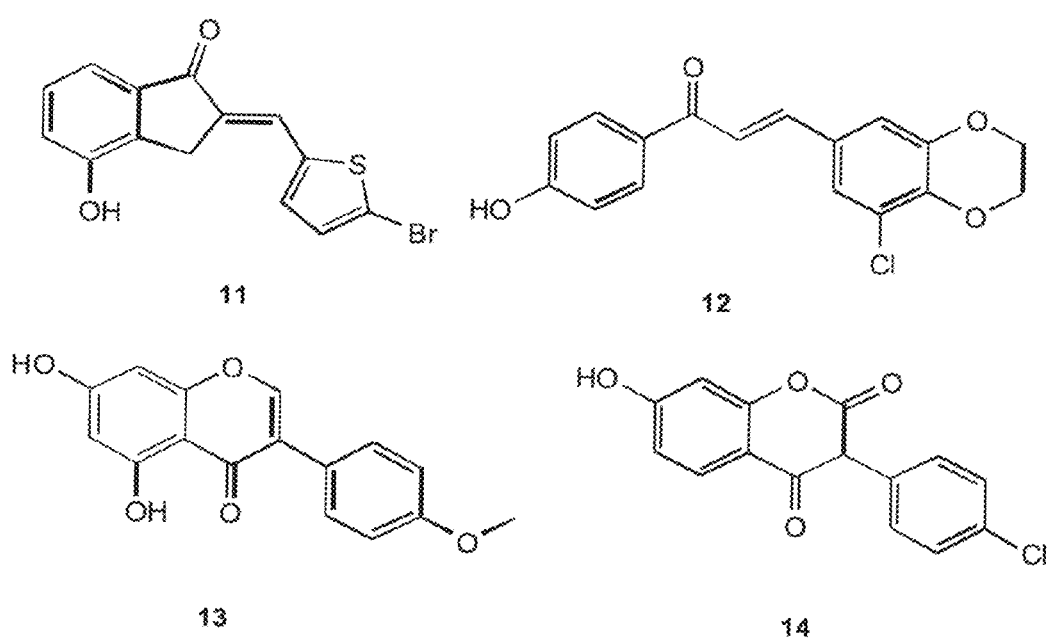
FIG. 3 shows examples of novel MAO-A inhibitors according to the present invention.
Figure 4A:
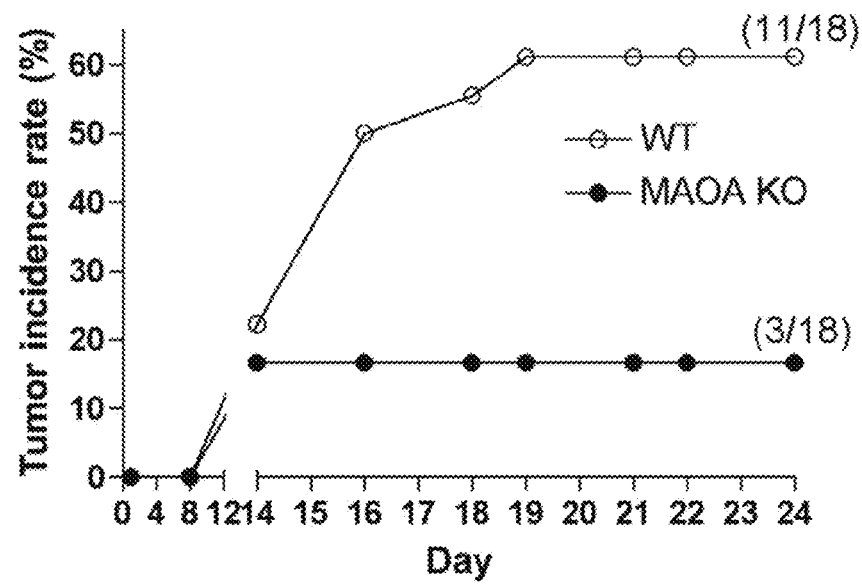
FIGS. 4A-4D show that MAO-A knockout in host impeded the growth of murine F9 teratocarcinoma xenograft. $1 \times 10^5$ murine F9 teratocarcinoma cells were subcutaneously injected into WT (N=9) and MAO-A KO (N=9) mice. *, $p<0.05$; **, $p<0.01$.
Figure 4B:
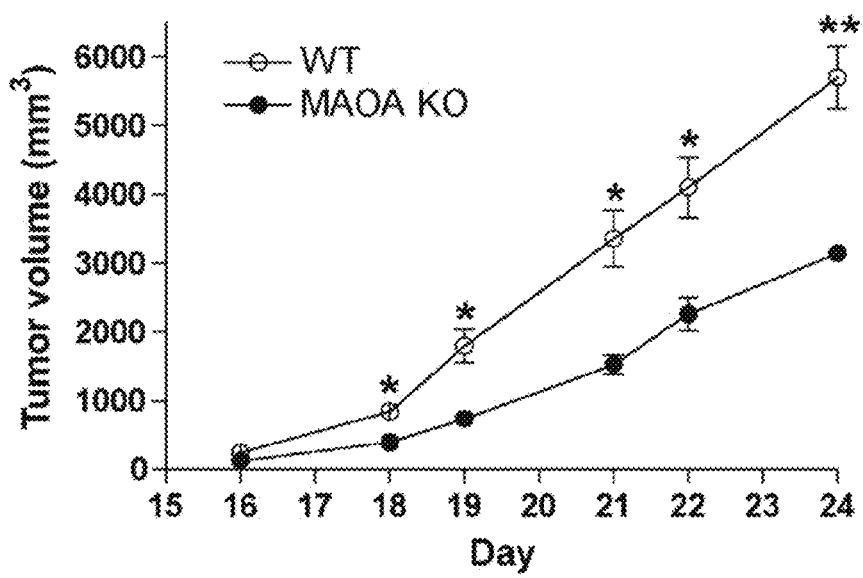
Figure 4C:
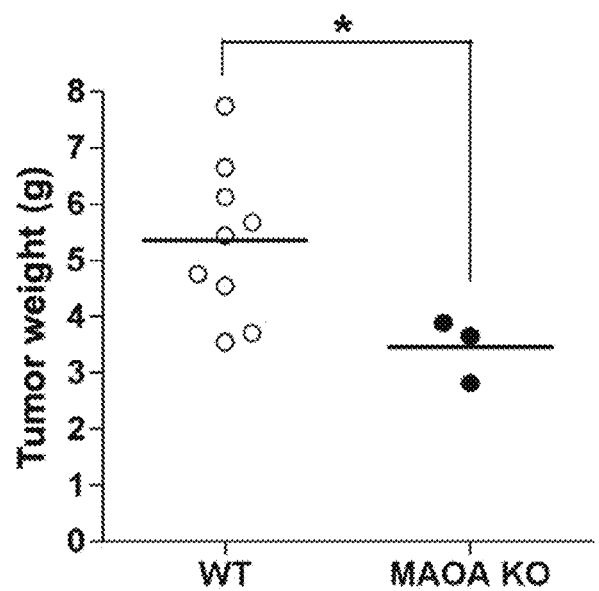
Figure 4D:
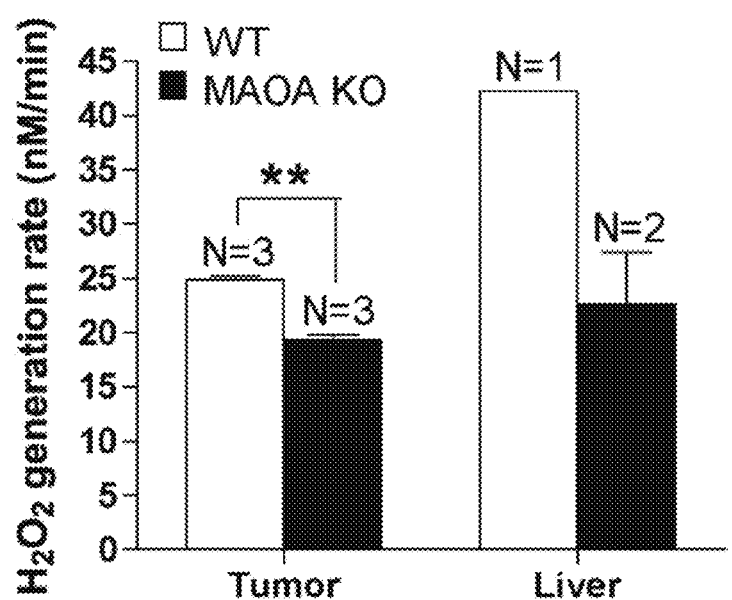
Figure 5A:
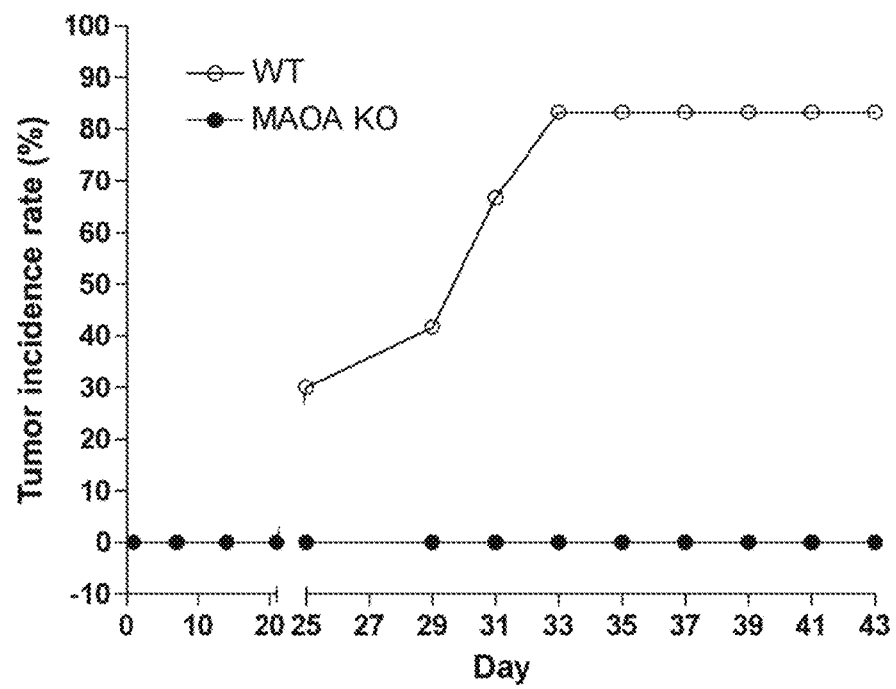
FIGS. 5A and 5B show that MAO-A knockout in host inhibited the growth of murine MCP3 prostatic carcinoma xenograft. $1 \times 10^5$ murine MCP3 prostatic carcinoma cells were subcutaneously injected into WT (N=4) and MAO-A neo KO (N=5) mice. *, $p<0.05$; **, $p<0.01$.
Figure 5B:
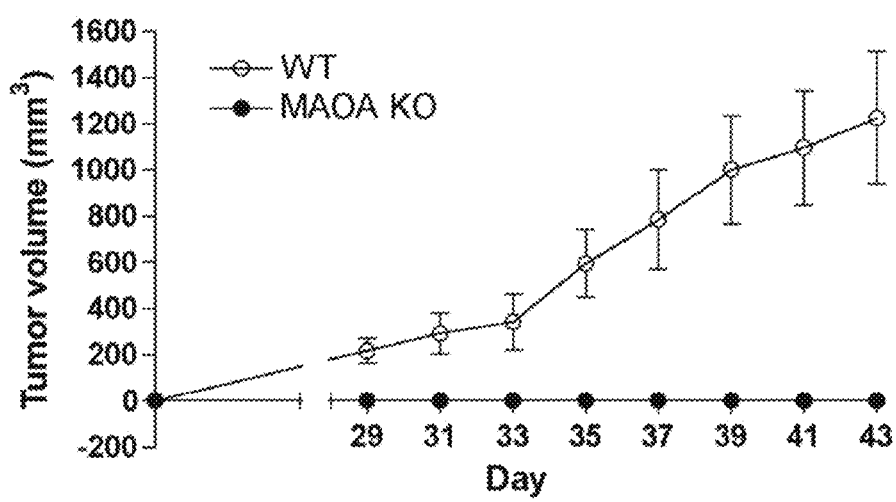
Figure 6:
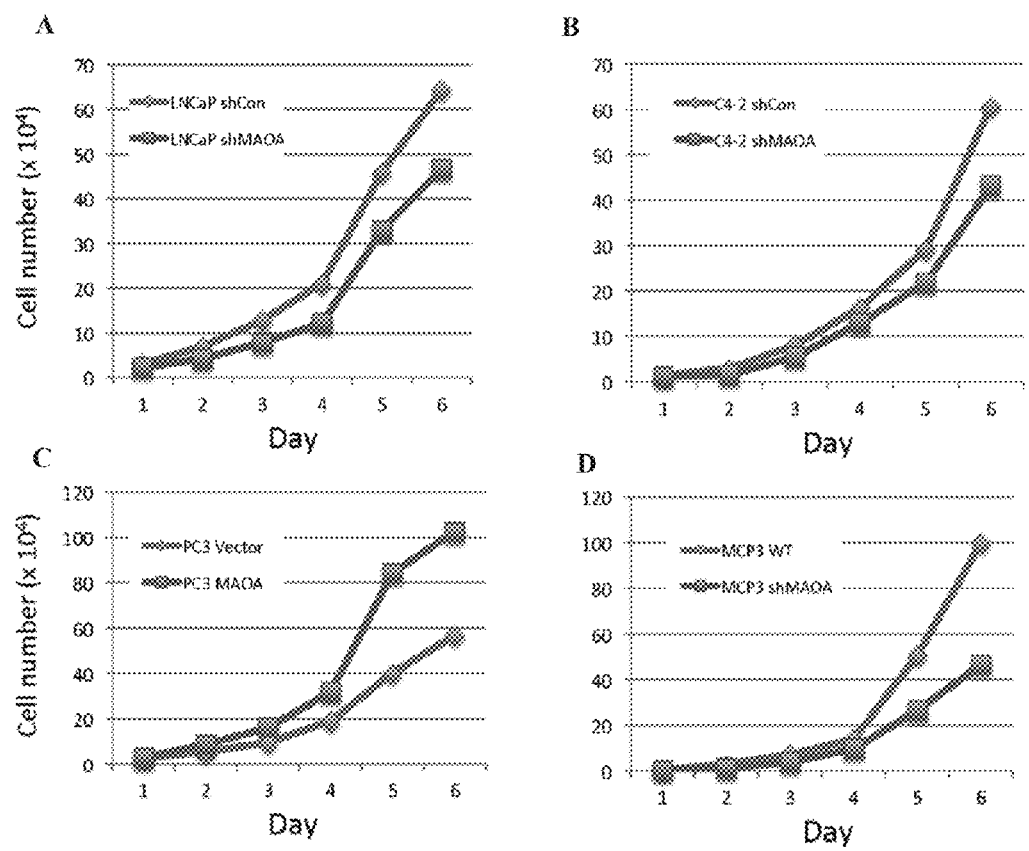
FIGS. 6A-6D show that MAO-A knockdown in murine MCP3 prostatic carcinoma cells inhibited the growth of tumor xenograft in vivo. $1 \times 10^6$ WT and MAO-A-KD murine MCP3 prostatic carcinoma cells were subcutaneously injected into 6 (WT cells) and 4 (MAO-A-KD cells) C57BL/6 mice, respectively. *, $p<0.05$.
Figure 7A:
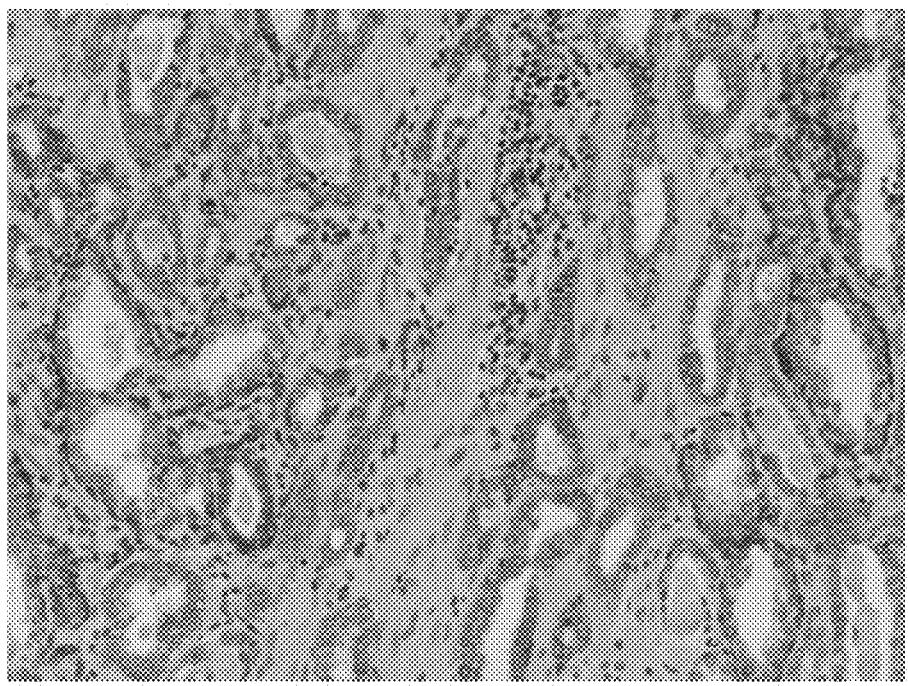
FIG. 7A, 7B, 7C, and 7D show that immunohistochemical staining of MAO-A and MAO-B in a tissue microarray consists of prostate cancer tissues from 88 patients (2 cores from each patient). 9A shows MAO-A, a basal cell protein, expresses in cancer cells; minimal stromal reaction in the benign and cancerous areas of the specimens. 9B, in contrast, shows MAO-B, a mesenchymal cell protein, was only minimally expressed in normal and cancerous prostate epithelial cells, but with increased expression in prostate cancer-associated stromal cells. Since prostate stromal cells are known to induce prostate cancer epithelial growth and progression, and clonal evolution of prostate epithelium, MAO-B could also be considered as an effective stromal target for therapeutic intervention. 9C shows intense MAO-A positive stained prostate cancer cells in human bone, suggesting MAO-A may be an excellent target for prostate cancer bone metastasis. 9D shows that normal prostate epithelial cells also expressed MAO-A but not MAO-B (data not shown).
Figure 7B:
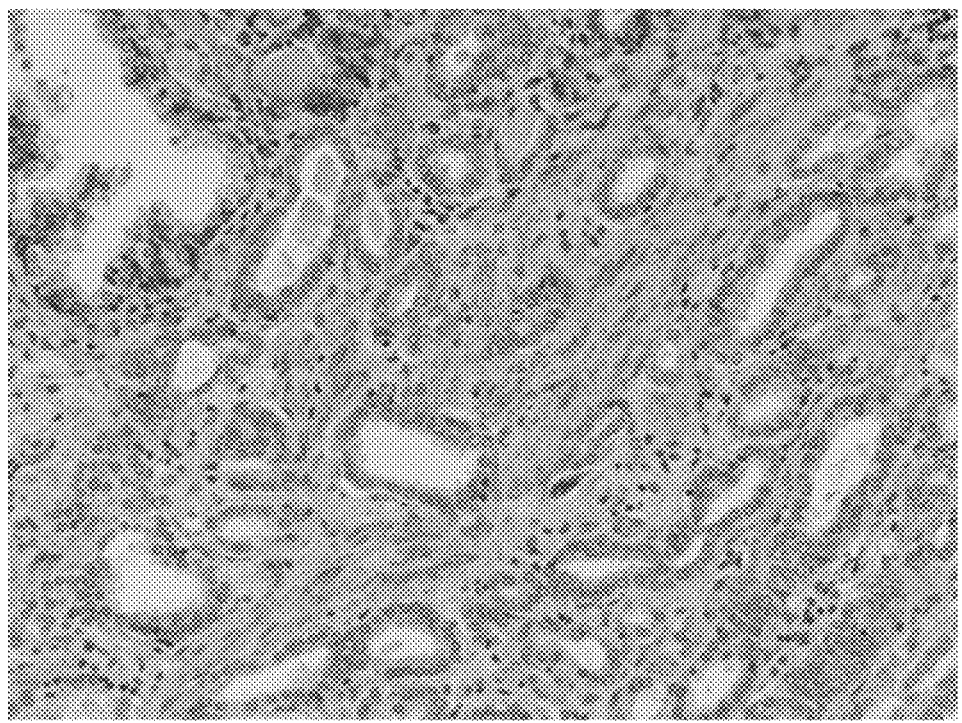
Figure 7C:
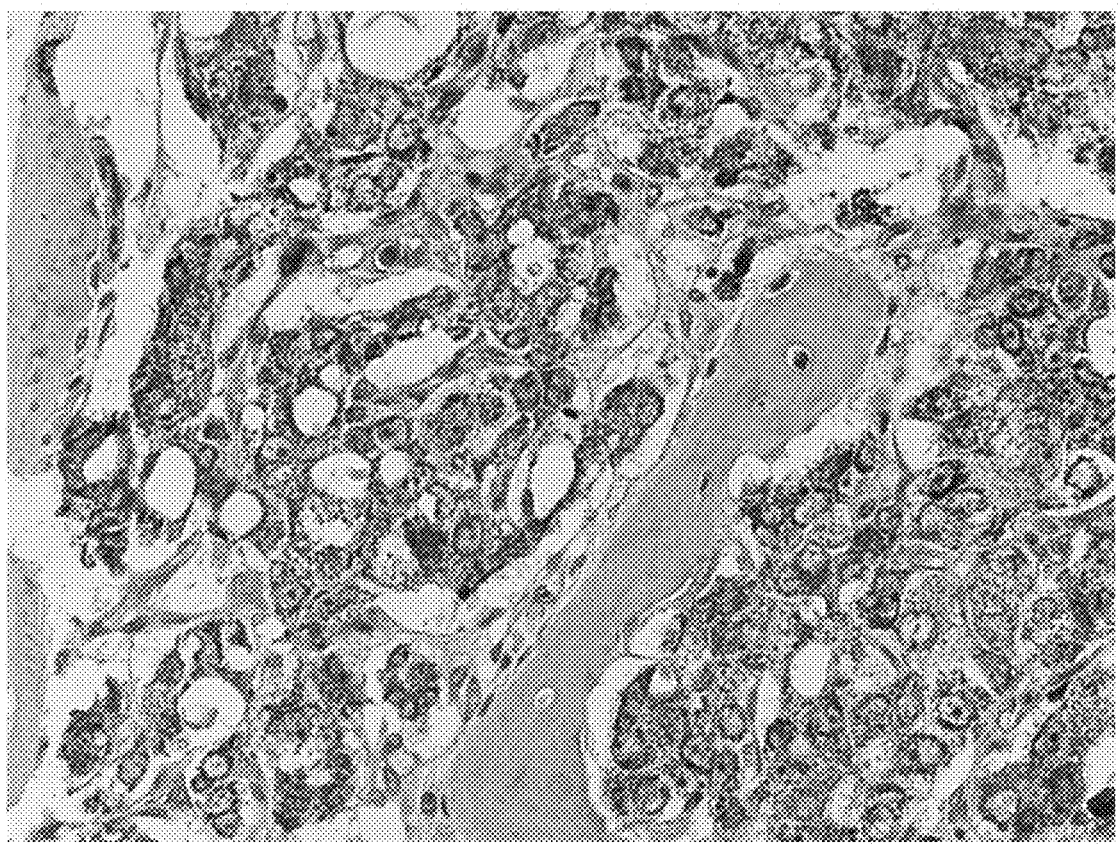
Figure 7D:
Figure 8:
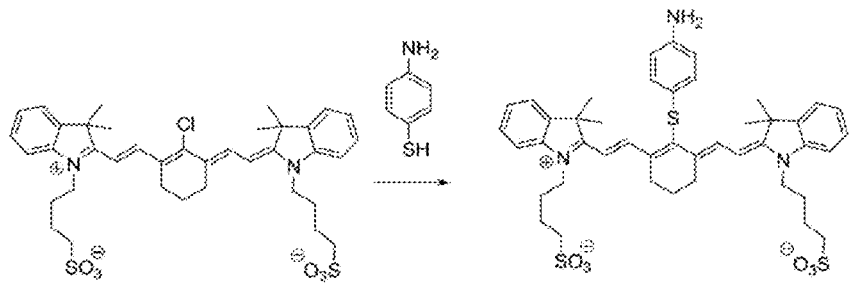
FIG. 8 shows a brief synthetic scheme of IR-783, a NIR dye, -docetaxel conjugate.
Figure 8:
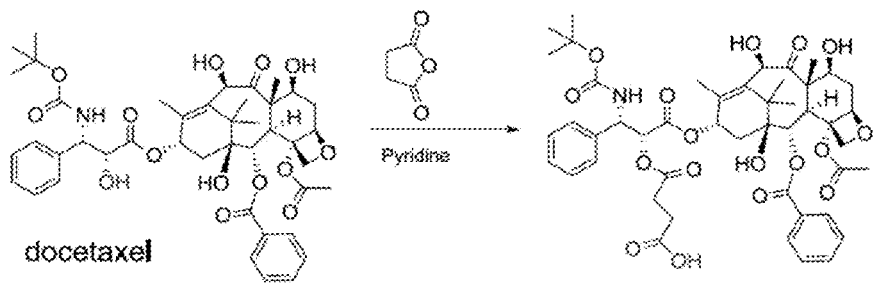
Figure 8:
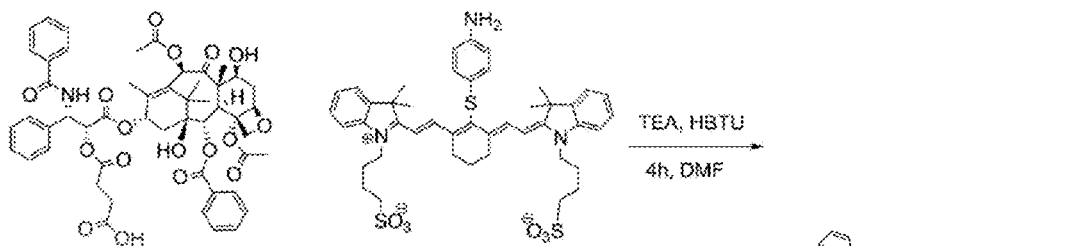
Figure 8:
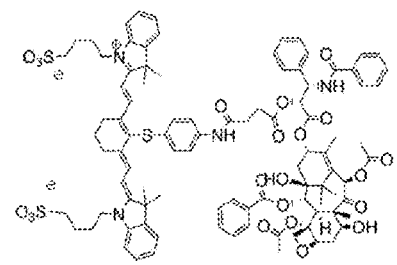
Figure 9C:
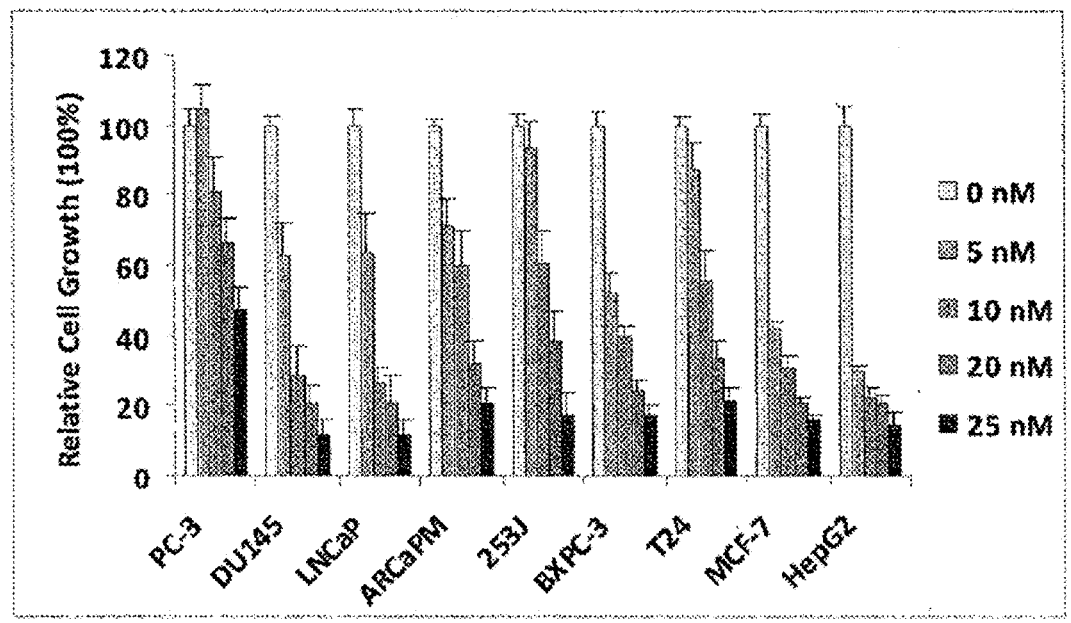
Figure 9D:
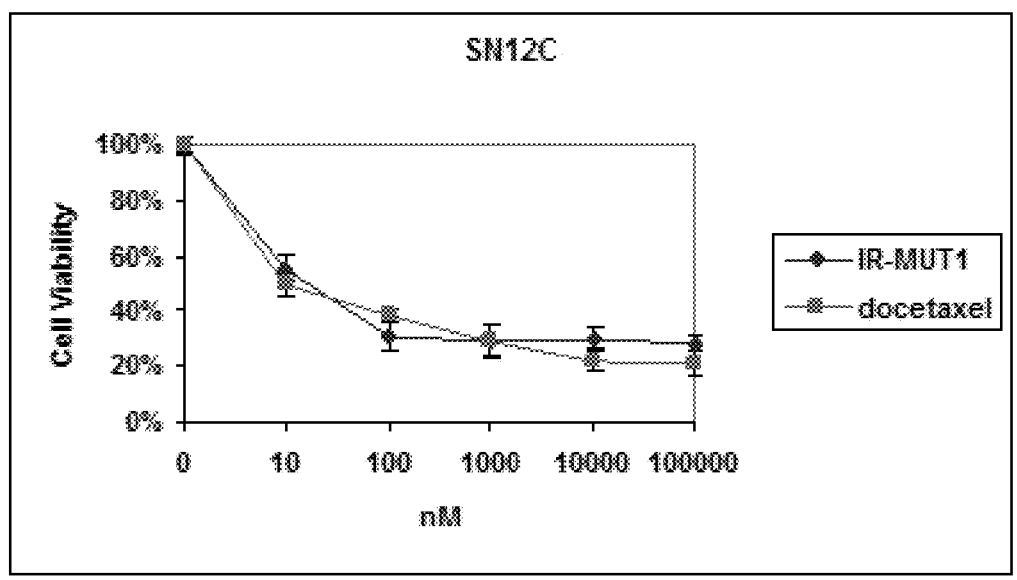
Figure 9E:
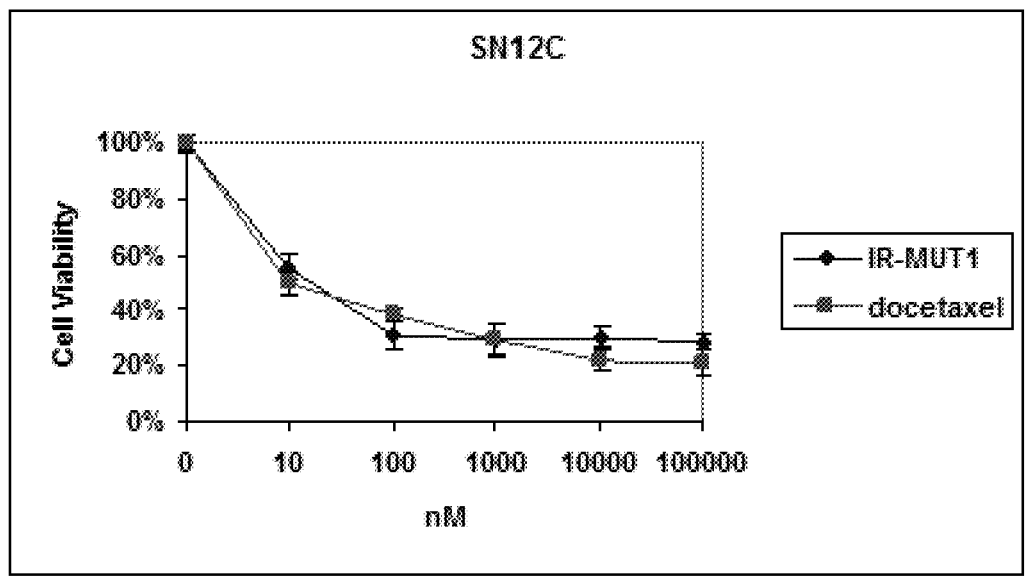

Preparation of clorgyline-dye conjugate. We have identified a class of near-infrared (NIR) fluorescent heptamethine cyanine dyes, IR-783 (1) (see FIG. 2), as a candidate for clorgyline conjugation. The near-infrared dye, IR-783, is commercially available and can be readily converted to precursor 3 in a single-step reaction with p-thioaniline 2. Based on our modeling studies with crystal structure of clorgyline-MAO-A complex [9], we determined that the amine nitrogen can be modified by the linker needed to conjugate this compound to precursor 3, but does not affects its inhibitory potency. The synthetic sequence for the preparation of the derivative clorgyline acid 9 is outlined in FIG. 2. The synthesis consists of a series of reductive amination reactions that yield from the commercially available propargylamine 4 and 3-(2,4-dichlorophenoxy)propanal 5. Conjugation of the two building blocks 3 and 9 can be accomplished by well-established sequence of synthetic steps. Similarly to IR-783, this conjugate is expected to have strong emission at 820-860 nm upon excitation at 750-780 mm. It can be easily read by NIR imaging.

Encapsulation of the clorgyline-dye conjugates in nanoparticles. In order to achieve water solubility of the clorgyline-dye conjugates and enhance their delivery to tumors, we will encapsulate them in calcium phosphate/silicate nanoparticles of average size of 22 nm that are freely dispersible in water [10]. This encapsulation process results only in minor changes to the photophysical properties of the dyes. Such an encapsulation method has been reported by Adair as effective means of delivery of hydrophobic dyes to cells [11]. Calcium phosphate is an excellent matrix for nanoparticle encapsulation because moderate concentrations of Ca$^{2+}$ ions are not toxic to cells and in vivo (found in human bone and teeth). It was shown that calcium phosphate dissolves below pH 5.5, liberating the cargo, but it is stable at pH 7.4 [12]. In addition, particles of this matrix disperse freely in aqueous media.

Typically, such nanoparticles are prepared using aqueous co-precipitation of calcium chloride and disodium hydrogen phosphate in the presence of disodium silicate within water-in-oil microemulsions [11, 13]. The encapsulation of the clorgyline-dye conjugate in nanoparticles will be accomplished through its addition into the microemulsion during precipitation. This process will yield nano-clorgyline as a colloidal suspension of nanoparticles of 22-30 nm in size. Its characterization will be done through analysis of the size distribution, morphology, and colloidal state of dispersion of the nanoparticle suspensions using transmission electron microscopy (TEM).

To determine the inhibition of MAO-A activity by nano-clorgyline. We will study the ability of nano-clorgyline to inhibit MAO-A activity by performing the inhibitory curves in human prostate cancel cell lines, LNCaP (non-metastatic cell line), C4-2 and ARCaPm, two metastatic cell lines. $IC_{50}$ will be determined. All these cell lines have moderate to high MAO-A activity. Shih's lab routinely performs MAO-A inhibition assay in vitro and in vivo.

To determine if nano-clorgyline is targeted to mitochondria of cancer cells. We will use laser-scanning confocal microscopy to determine cellular uptake and localization of the nano-clorgyline within cells. The near-infrared dye moiety within the conjugate will serve as a directing group, guiding the conjugate to mitochondria. It has been shown that redox potential of mitochondria is different between cancer and normal cells.

Human cancer cell lines (LNCaP, non-metastastic cell line, C4-2, $ARCaP_M$, two metastastic cell lines), will be tested. As negative controls, normal human prostate epithelial cells (P69 and NPE), normal human prostate fibroblasts (NPF), will be used.

It is anticipated the following studies will show that the growth of prostate cancer will be significantly reduced after the treatment with nano-clorgyline. The outcome will be determined by reduced tumor growth in rate, size and weight. We expect nano-clorgyline will be more effective with fewer side effects than clorgyline itself. In addition, we will establish MAO-A as a biomarker for prostate cancer, with nano-clorgyline to be used for diagnostic tool; further, we will follow the progression of prostate cancer during treatment through imaging of the uptake of the nano-clorgyline.

2. MHI Dye Nanoparticle Conjugate

Synthesis of MHI-corgyline: MHI-clorgyline has been prepared through a series of synthetic steps by conjugating dye MHI-148 and clorgyline as outlined in FIG. 10. A linker of proper length was designed to minimize negative impact of the dye on the inhibitory potency of clorgyline.

Preparation of MHI-clorgyline started with commercially available 2,4-dichlorophenol 1. This compound was alkylated under standard conditions (NaOH, $H_2O$) with 1,3-dibromopropane. The product 2 was then reacted with $NaN_3$ in DMF to yield the azide 3, which was subjected to the next step as a solution in MTBE without further purification. The solution of 3 was hydrogenated under low $H_2$ pressure using Pd on activated charcoal as a catalyst in the presence of $Boc_2O$ and resulting in the formation of the carbamate 4. This compound was alkylated with propargyl bromide using NaH in dry DMF, producing Boc-protected alkyne 5. The Boc protecting group was removed under acidic conditions using TFA in DCM. The product 6 was alkylated again with 1-bromo-3-thioacetylpropane 7, resulting in the formation of 8, albeit in low yield. Removal of the acetyl protective group was carried out in methanolic HCl and afforded intermediate 9. This intermediate was then coupled with MHI-148 dye using EDC and 4-DMAP to afford the product MHI-clorgyline 10. This product was purified using reverse-phase HPLC and its identity was confirmed by mass spectrometry.

Imagining of MHI-clorgyline in live cells: Previous study showed that the near-IR hepatamethine cyanine dyes IR-783 and MHI-148 can be retained in cancer cells but not normal cells in tumor xenografts and in spontaneous tumors in transgenic mice. Moreover, the two dyes also have strong emission at 820-860 nm upon excitation at 750-780 nm, which can be easily detected and visualized by NIR imaging equipment and laser-scanning confocal microscopes. Here, we resorted to the use of Zeiss LSM 510 confocal microscope as the imaging equipment. Although cellular uptake of the conjugate was uncertain, due to the similarity in structure, MHI-clorgyline conjugates were expected to have similar fluorescence properties as the NIR dye itself. Therefore, NIR imaging with laser-scanning confocal microscope was used to examine the cellular uptake of MHI-clorgyline in human prostate epithelial cancer cells (C4-2B). This cell line was selected due to its high levels of the expressed MAO-A.

In the preliminary study we found that IR-783 dye co-localized in mitochondria of the live cells. An imaging study with the newly synthesized MHI-clorgyline 10 was carried out (FIG. 11). This compound also showed rapid accumulation in C4-2B PCa cells and was localized in the mitochondria, as determined by the co-staining with mitochondria-specific dye.

In order to test an inhibitory activity of the MHI-clorgyline 10, a standard MAO A inhibition assay was carried out in C4-2B cells using radiolabeled substrates. The results clearly indicate that our designed conjugate 10 inhibits MAO A activity with mean $IC_{50}$ of $2.18\times10^{-5}$ M (FIG. 12). The activity of the conjugate 10, while lesser than that of clorgyline itself (data not shown), is sufficient for the in vivo studies, which are currently ongoing.

The Function of the Nano-clorgyline In Vivo—its Location and Inhibition of Tumor Growth in Mice To study the location of nano-clorgyline, and its effect on tumor progression in mice. We will inject human LNCAP non-metastatic prostate cancer cells ($1\times10^6$) into immuno-deficient nude mice with (1) nano-clorgyline, concentration required to inhibit nearly 100% of MAO-A activity using results from Specific Aim 1b; (2) clorgyline itself (positive control, 10 mg/kg for 100% inhibition of MAO-A activity); (3) dye itself (negative controls, same concentration as nano-clorgyline). A total of 18 mice is required for this part of the study (6 per each group).

Then, we will image the tumor location, monitor the tumor growth (size, number) every other day for one month. The tumor will be located by NIR imaging. The Olenyuk lab has an extensive experience in NIR imaging and the needed equipment is available at the Norris Cancer Center. If our hypothesis is correct, the nano-clorgyline will be located in prostate cancer, and the tumor growth will be reduced. At the end of 30 days, the mice will be sacrificed, the MAO-A activity will be determined in the tumor (if there is still tumor) and the normal prostate tissues. See FIG. 1 in prior work for details of this experiment). This study will demonstrate the potential useful of nano-clorgyline for diagnosis and therapy.

To study the effect of nano-clorgyline on the metastasis of prostate cancer in mice. Human prostate cancer cells with metastatic potential will be injected to mice, human C4-2, ARCaPm, ($1\times10^6$ cells), same three group of mice will be used, the procedure and the experiments will be the same as described in Specific Aim 2a. The tumor growth rate and size and locations will be determined. The presence of absence of the tumor in the bone, will be examined and as an indication of metastasis. A total of 36 mice will be used (18 mice per each cell line with 3 groups of treatment; 2 metastatic cell lines).

The effects of nano-clorgyline alone or in combination with the existing treatments on tumor growth and metastasis in mice.

First line treatment for advanced prostate cancer is androgen ablation therapy (ADT). Unfortunately the duration of response to ADT is limited (about 18 months) and the patients eventually develop castration resistance. The first line treatment for patients with castration resistant PCA is usually chemotherapy with the microtubule inhibitor, docetaxel. Recently, FDA approved the specific CYP17 inhibitor, abiraterone, for the treatment of castration resistant patients who fail docetaxel therapy. This study will evaluate the effects of nano clorgyline alone or in combination with one of these treatment approaches on tumor growth. Since the nano clorgyline can be read non-invasively by INR imaging, the prognosis of each treatment can be easily determined.

Human LNCAP cells (non-metastatic prostate cancer cell line). Alternatively, ARCaPm (with potential for metastasis) will be injected to immunodeficient nude. Next, mice will be divided to three groups as described in A. The tumor location, size, number of lesions will be determined every other day from day 1 to day 30. On day 31 mice will be sacrificed, tumor and host MAO Activity will be determined.

| A: | (Group I) | nano-chlorgyline (1 mg/kg*) with androgen ablation therapy (castration)** |
|---|---|---|
| | (Group II) | nano-chlorgyline alone (1 mg/kg*) |
| | (Group III) | castration alone** |
| B: | (Group I) | docetaxel (daily, 15 mg/kg) |
| | (Group II) | nano-chlorgyline alone 1 mg/kg*), |
| | (Group III) | docetaxel (15 mg/kg), nano-chlorgyline (1 mg/kg*) |
| C: | (Group I) | new drug (abiraterone, 180 mg/kg) daily |
| | (Group II) | nano-chlorgyline alone (1 mg/kg*), |
| | (Group III) | new drug (abiraterone, 180 mg/kg) and nano-clorgyline 1 mg/kg*) |

*The concentration of nano-clorgyline to be used will be adjusted based on the results obtained from specific aim 1b.

For the castration group, trans-scrotal castration will be performed under isoflurane anesthesia with proper aseptic and antiseptic technique. A total of 108 mice will be used. Synthesis of Nanoparticle Conjugates with Other Novel MAO-A Inhibitors Obtained from High Throughput Screening.

Optionally, other novel MAO-A inhibitors, disclosed herein may be conjugated for use in the methods and treatments of the present invention. Specifically, below are examples of four high affinity novel MAO-A inhibitors 11-14. They may be conjugated with the near-infrared dye, such as IR-783. The phenol functionality (—OH) presents a viable choice for linker attachment and the subsequent derivatization of these molecules with fluorescent precursor 3 in order to generate novel nanoparticle based MAO-A inhibitors.

MAO-A Confers Prostate Cancer EMT by Stabilizing H1F1α and Enhancing VEGF-mediated Twist1 Activation High Gleason grade prostate carcinomas are aggressive, poorly differentiated tumors that exhibit elevated MAO-A expression. We have found that a key function of MAO-A is to promote an epithelial-to-mesenchymal transition (EMT). EMT is the process of cellular development characterized by loss of cell adhesion, repression of E-cadherin expression, and increased cell mobility. In the context of cancer, promotion of EMT correlates with the increased cell invasion, migration and metastatic potential, hence, the EMT-promoting effect of MAO-A connects MAO-A activity to cancer. More specifically, we have found that overexpression of MAO-A in human prostate cancer cells induces the loss of E-cadherin (an epithelial marker), up-regulates Vimentin/N-cadherin (mesenchymal markers) and increases cell migration and invasion Conversely, knockdown of MAO-A impedes EMT in human prostate cancer cells.

Without being bound to any particular theory, we offer the following experimental observations (FIGS. 20-26). to explain in mechanistic terms the corrections between MAO-A activity and its various cancer promoting effects.

Figure 27:
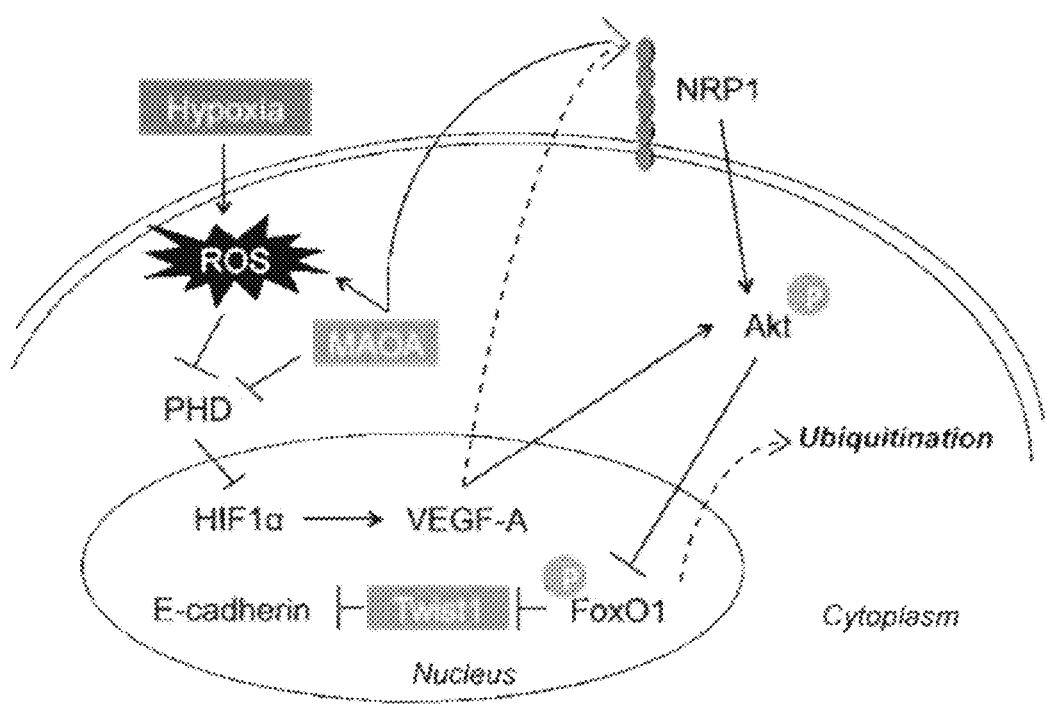
FIG. 27 shows a schematic representation of the MAO-A driven EMT mechanism.

First, we found that MAO-A enhances HIF1α stability by reducing prolyl hydroxylase (PHD) activities and increasing intracellular ROS levels. We then found that by treating prostate cancer cells with a ROS scavenger (N-acetylcysteine), MAO-A-induced HIF1α expression is diminished, which in turn, also decreased MAO-A-enhanced cell proliferation. Moreover, we also found that MAO-A mediated the activation of VEGF and its receptor Neuropilin-1 (NRP1) in response to hypoxia, which in turn stimulated the Akt/FoxO1 signaling pathway and reduced FoxO1 activity by promoting its phosphorylation followed by nuclear export. We further discovered that FoxO1 acts as a transcriptional repressor of Twist1 and binds to a response element in the proximal region of Twist1 promoter. Twist1 is known to be an oncogene in several cancers and is involved in tumor metastasis. FIG. 27 summarizes the mechanism.

Importantly, this mechanism is manifested in high Gleason grade cancers, which exhibit significantly more HIF1α, VEGF and Twist1 expression, but less FoxO1 nuclear localization compared to low Gleason grade cancers. Therefore, expression levels of MAO-A, HIF1α, VEGF and Twist1 serve as a biomarker for objectively differentiating high Gleason grade cancers from low Gleason grade cancers.

EXAMPLES

The following examples are provided in order to demonstrate and further illustrate certain embodiments and aspects of the present invention and are not to be construed as limiting the scope thereof. While such examples are typical of those that might be used, other procedures known to those skilled in the art may alternatively be utilized. Indeed, those of ordinary skill in the art can readily envision and produce further embodiments, based on the teachings herein, without undue experimentation.

Example 1

MAO-A KO in Host Experiment 1: Murine F9 Teratocarcinoma Tumor Xenograft in WT and MAO-A KO Mice Cell # injected: $1\times10^5$ Mice #: WT (N=9) and MAO-A KO (N=9) Tumor injection site #: WT ($2\times9=18$) and MAO-A KO ($2\times9=18$) Tumor incidence rate: WT (11/

18=61.1%) and MAO-A KO (3/18=16.7%) Tumor growth: WT>MAO-A KO (p<0.05) Tumor weight: WT>MAO-A KO (p<0.05)

Example 2

MAO-A KO in Host Experiment 2: Murine MCP3 (pten/p53 Double KO) Prostatic Tumor Xenograft in WT and MAO-A KO Mice Cell # injected: $1 \times 10^6$ Mice #: WT (N=3) and MAO-A KO (N=3) Tumor injection site #: WT (4×3=12) and MAO-A KO (4×3=12) Tumor incidence rate: WT (11/12=91.7%) and MAO-A KO (10/12=83.3%) Tumor growth: WT>MAO-A KO (p<0.05) Tumor weight: WT>MAO-A KO (p=0.25)

Example 3

MAO-A KO in Host Experiment 3: Murine MCP3 Prostatic Tumor Xenograft in WT and MAOA KO Mice Cell # injected: $1 \times 10^5$ Mice #: WT (N=4) and MAO-A KO (N=5) Tumor injection site #: WT (3×4=12) and MAO-A KO (3×5=15) Tumor incidence rate: WT (10/12=83.3%) and MAO-A KO (0/15=0) Tumor growth: No MCP3 tumor growth in MAO-A KO mice

Example 4

MAO-A KD in Tumor Experiment 1: Murine WT and MAO-A-Kb MCP3 Prostatic Tumor Xenograft in C57BL/6 Mice Cell # injected: $1 \times 10^6$ Mice #: Mice for WT MCP3 cells (N=6) and mice for MAO-A-KD MCP3 cells (N=4) Tumor injection site #: WT MCP3 cells (4×6-24) and MAO-A-KD MCP3 cells (4×4=16) Tumor incidence rate: WT MCP3 cells (21/24=87.5%) and MAO-A-KD MCP3 cells (0/16=0) Tumor growth: With MAO-A KD in tumor, there is no tumor growth.

Example 5

MAO-A KD in Tumor Experiment 2: Murine WT and MAO-A-KD MCP3 Prostatic Tumor Xenograft in C57BL/6 Mice Cell # injected: $1 \times 10^6$ Mice #: Mice for WT MCP3 cells (N=6) and mice for MAO-A-KD MCP3 cells (N=6) Tumor injection site #: WT MCP3 cells (3×6=18) and MAO-A-KD MCP3 cells (3×6=18) Tumor incidence rate: As of July 16, WT MCP3 cells (15/18=83.33%) and MAO-A-KD MCP3 cells (0/18=0).

Example 6

Synthesis of MHI-clorgyline and the Role of MAO-A in Prostate Cancer Progression General Synthesis: All reagents and solvents were obtained from commercial sources and were used as received unless otherwise stated. All reactions involving moisture-sensitive reagents were conducted under argon atmosphere with anhydrous solvents and flame-dried glassware. Hygroscopic liquids were transferred via a syringe and were introduced into reaction vessels through rubber septa. Reaction product solutions were concentrated using a rotary evaporator at 30-150 mm Hg. Column chromatography was performed on silica gel (230-400 mesh) using reagent grade solvents. Analytical thin-layer chromatography (TLC) was performed on glass-backed, pre-coated plates (0.25 mm, silica gel 60, F-254, EM Science). Analytical HPLC were performed on Microsorb-MV $C_8$ reverse-phase column (250×4.6 mm, Varian) using Shimadzu LC-10A VP pump and Shimadzu SPD 10A VP UV-vis variable-wavelength detector. Preparative HPLC purifications were carried out with $C_8$ reverse phase preparative column (Grace Davison). The flow rate for preparative reverse-phase HPLC was 4 mL/min. In all cases, 5%-95% gradients of acetonitrile in 0.1% aqueous trifluoroacetic acid (TEA) were used as eluents. Water (18 MΩ) was obtained from a Barnstead water purification system, and all buffers were 0.2 μm filtered. Nuclear magnetic resonance (NMR) spectra were collected on Varian 400 MHz instruments in the indicated solvents. The peak positions are reported with chemical shifts (δ) in parts per million (ppm) downfield from the signal for tetramethylsilane (0 ppm) and referenced to the signal resulting from the incomplete deuteration of a solvent used in the experiment ($CDCl_3$: 7.26 ppm, or the center line of the multiplet of $DMSO-D_6$: 2.50 ppm). Carbon-13 chemical shifts are reported as δ values in ppm and referenced to the carbon-13 signal of a solvent used in the experiment ($CDCl_3$: 77.0 ppm, or the center line of the multiplet $DMSO-D_6$: 39.51 ppm). The coupling constants (J) are reported in Hertz (Hz). The following abbreviations are used: singlet (s), doublet (d), triplet (t), doublet of doublets (dd), multiplet (m). Mass spectra were obtained from the Agilent 6520 time-of-flight mass spectrometer.

(1) Synthesis of MHI-Clorgyline

Synthesis of 1-(3-bromopropoxy)-2,4-dichlorbenzen (2)

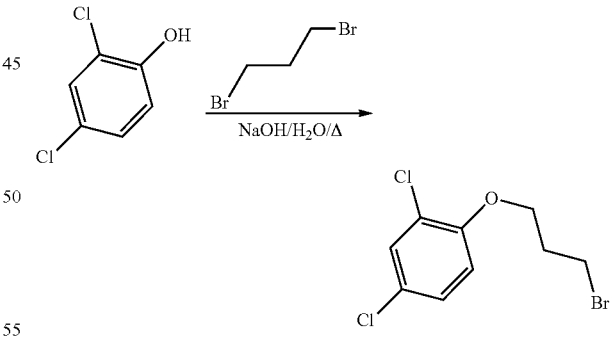

A mixture of 2,4-dichlorophenol 1 (4.1 g, 25 mmol), 1,3-dibromopropane (10 g, 50 mmol) and a solution of sodium hydroxide (1.0 g) in water (4 mL) was stirred at reflux for 1.5 h. A solution of sodium hydroxide (1.0 g) in water (6 mL) was added and the mixture was refluxed for an additional 1.5 h. After cooling, the reaction mixture was extracted with chloroform (50 mL) and washed with water (30 mL×3). The organic layer was dried over sodium sulfate and evaporated in vacuo. Crude product was obtained (10.49 g) and then purified by silica gel column (79.16 g). Yield 10.7% (0.794 g).

Synthesis of 1-(3-azidopropoxy)-2,4-dichlorobenzene (3)

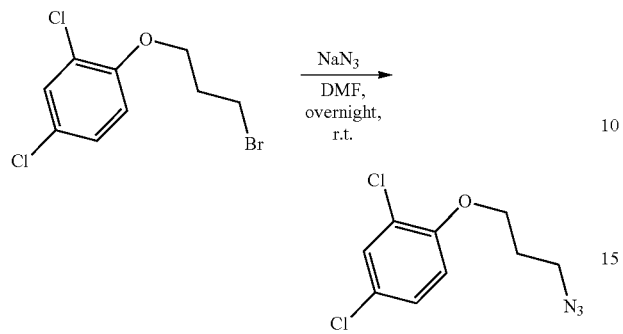

To a solution of 1-(3-bromopropoxy)-2,4-dichlorobenzene (600 mg, 2.11 mmol) in 6.0 mL DMF in a 25 mL round-bottom flask equipped with a stir bar, a thermocouple in a thermowell and a rubber septum stopper with sleeve, 234.0 mg (3.60 mmol) of $NaN_3$ was added at room temperature. Under $N_2$ pressure, the mixture was stirred overnight. The formation of off-white suspension was observed. 20 μL, of the reaction mixture was partitioned with 0.5 mL MTBE and 0.5 mL water, and the MTBE layer was used for TLC (silica gel, 100% hexane). The rest of the reaction mixture was partitioned with MTBE and water. The water layer was washed by MTBE. The MTBE layer were washed sequentially with water and $NaHCO_3$, and then used in the next step without further purification.

Synthesis of tert-butyl 3-(2,4-dichlorophenoxy)propylcarbamate (4)

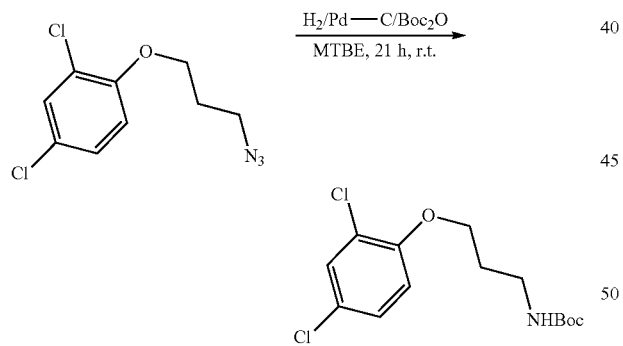

The MTBE layer obtained from the previous step was transferred into a 500 mL round-bottom flask equipped with a stir bar and a rubber septum stopper with sleeve. In $N_2$ atmosphere, $Boc_2$ (571.0 mg, 2.616 mmol) and Pd/C (518 mg) was added. $N_2$ was carefully replaced by $H_2$. A rubber balloon was used to keep the system under positive gas pressure. TLC (silica gel, 100% hexane to detect starting material and MTBE: hexane=1:1 to detect the product, ninhydrin stain) was used to follow the process of the reaction. Under $N_2$ pressure, the mixture was stirred for 21 h. The reaction mixture was filtered under vacuum through glass microfiber and Celite 545. The filtrate was partition by MTBE and water. The water layer was washed by MTBE. The MTBE layers were washed sequentially with water, saline and $NaHCO_3$, dried by $MgSO_4$, filtered and evaporated. Crude product (991.2 mg) was obtained after work up and purified by silica gel column. Yield 11.4% (77.3 mg).

Synthesis of tert-butyl 3-(2,4-dichlorophenoxy)propyl(prop-2-ynyl)carbamate (5)

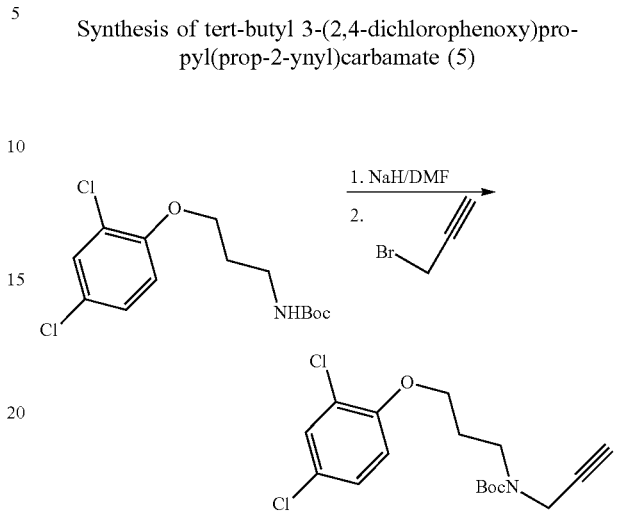

To a solution of tert-butyl 3-(2,4-dichlorophenoxy)propylcarbamate (77.3 mg, 0.24 mmol) in 0.8 mL DMF in a 20 mL vial equipped with a stir bar and a rubber septum stopper with sleeve and under Ar pressure, NaH (11.9 mg, 0.30 mmol) was added with cooling by ice bath. The reaction mixture was kept under Ar atmosphere at all times. Propargyl bromide in toluene (44.5 mg, 0.30 mmol) was added. The reaction mixture was stirred at room temperature. Next, a small portion of the reaction mixture (10-15 μL) was partitioned with 350 μL MTBE and 350 μL water, and the MTBE layer was used for TLC (silica gel, hexane:MTBE=1:1). The rest of the reaction mixture was partitioned with 20 mL MTBE and 20 mL water. The water layer was washed by 20 mL MTBE. The MTBE layers were washed sequentially with water, saline and $NaHCO_3$, dried by $MgSO_4$, filtered and evaporated. Crude product was purified by silica gel column (1.23 g). Yield 27.4% (23.7 mg).

Synthesis of N-(3-(2,4-dichlorophenoxy)propyl)prop-2-yn-1-aminium 2,2,2-trifluoroacetate (6)

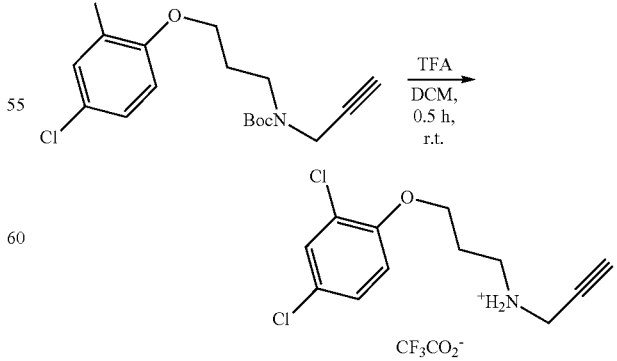

To a solution of tert-butyl 3-(2,4-dichlorophenoxy)propyl (prop-2-ynyl)carbamate (23.7 mg, 66.1 µmol) in 600 µL DMF in a 20 mL vial equipped with a stir bar, 600 µL TFA was added at room temperature while stirring. In 0.5 h, TLC (MTBE:hexane=1:1, ninhidrin stain) indicated the completion of the reaction. The volatiles were evaporated. The residue was co-evaporated with ACN for 3 times and then used in the next step without further purification.

Structure of the product was proved by NMR and LC-MS.

Synthesis of S-3-bromopropyl ethanethioate (7)

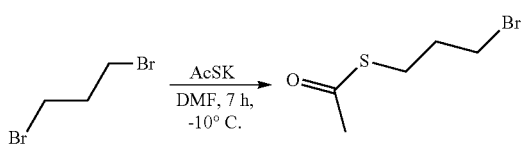

A 250 mL three-neck round-bottom flask equipped with a thermocouple in a glass sleeve, a magnetic stirrer, a vigreux column with an Argon inlet (middle stem) and a sleeved rubber septum stopper was assembled and dried with a heat gun under flow of Ar. Approximately 110-120 mL of anhydrous DMF was added via cannula under Ar. AcSK (11.68 g, 102.3 mmol) was added by portions into the flask while cooled with ice-MeOH bath. The reaction went on for 7 h at about −10° C. The ice-MeOH bath was removed after quenching the reaction by adding 165 mL water. The reaction mixture was partitioned with 300 mL MTBE and 700 mL water. The water layer was washed by 200 mL MTBE. The MTBE layers were washed sequentially with water, saline and NaHCO₃, dried by MgSO₄, filtered and evaporated. Yield 98.7% (19.1 g).

Synthesis of S-3-43-(2,4-dichlorophenoxy)propyl) (prop-2-ynyl)amino)propyl ethanethioate (8)

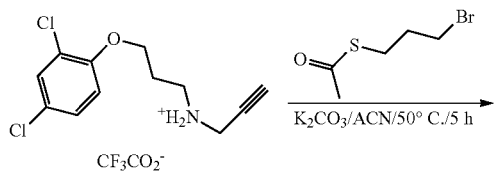

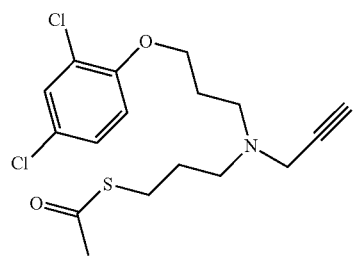

To a solution of N-(3-(2,4-dichlorophenoxy)propyl)prop-2-yn-1-aminium 2,2,2-trifluoroacetate (2.14 mg, 0.05 mmol) in 100 µL ACN in a 5 mL vial equipped with a stir bar, 12.1 mg (0.09 mmol) of K₂CO₃ and 142.4 mg (0.720 mmol) S-3-bromopropyl ethanethioate was added. The mixture was stirred while heated to 50° C. in an oil bath. TLC was performed (silica gel, MTBE:hexane=9:1 to detect starting material and MTBE:hexane=1:9 to detect the consumption of the thioacetate reagent) to follow the process of the reaction. To a solution of N-(3-(2,4-dichlorophenoxy)propyl)prop-2-yn-1-aminium 2,2,2-trifluoroacetate (17.1 mg, 0.05 mmol) in 800 µL ACN in a 20 mL vial equipped with a stir bar, 120.0 mg (0.870 mmol) of K₂CO₃ and 95.2 mg (0.48 mmol) S-3-bromopropyl ethanethioate was added. The mixture was stirred while heated by 50° C. oil bath for 5 h. The reaction mixtures of the two reactions were combined, filtered and evaporated. Crude product (168.4 mg) was obtained and co-evaporated with hexane for 3 times to remove ACN. Silica gel column (1.25 g) was used to purify the crude product. Yield 14% (2.6 mg).

Structure of the Product was Proved by NMR and LC-MS

Synthesis of 3-((3-(2,4-dichlorophenoxy)propyl) (prop-2-ynyl)amino)propane-1-thiol (9)

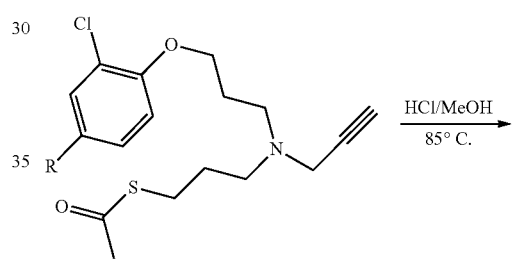

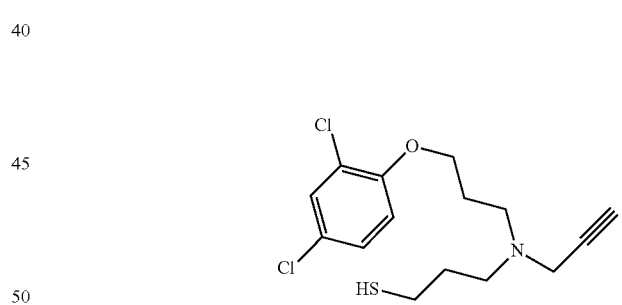

A solution of S-3-((3-(2,4-dichlorophenoxy)propyl) (prop-2-ynyl)amino)propyl ethanethioate (1.17 mg, 3.10 µmol) in 200 µL ACN was added into a 20 mL vial equipped with a stir bar, evaporated and then co-evaporated with MeOH for 3 times to remove ACN. MeOH/HCl (200 µL) was added into the vial and then the vial was heated by 85° C. oil bath for 6 h. The reaction mixture was evaporated, co-evaporated sequentially by MeOH for 3 times and ACN for 3 times, and then used in the next step without further purification.

Synthesis of MHI 148-clorgyline Conjugate (10)

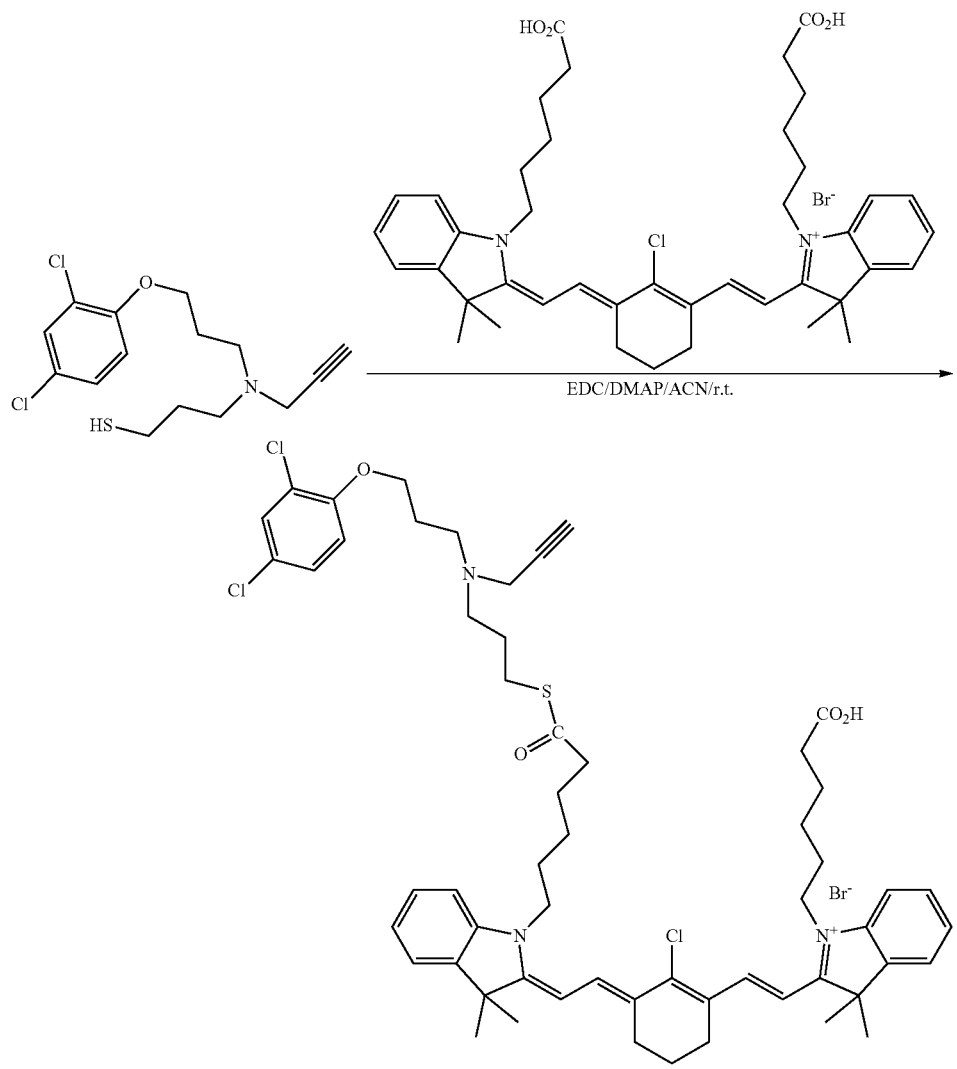

MHI-148 (4.7 mg, 6.2 mmol) and EDC (1.5-2.4 mg, 7.8-12 mmol), followed by 1.5 mg of DMAP (12 mmol) were added into a 20 mL vial equipped with a stir bar. ACN (400 µL) was added to make solution. The reaction mixture of the previous step was transferred dropwise to the vial with 200 µL it ACN at room temperature. The reaction mixture was purified by HPLC (GRACE Davison Apollo $C_8$ 5 u column, 250 mm×10 mm).

Mechanistic Investigation of the Role of MAOA in PCa Progression

Figure 13:
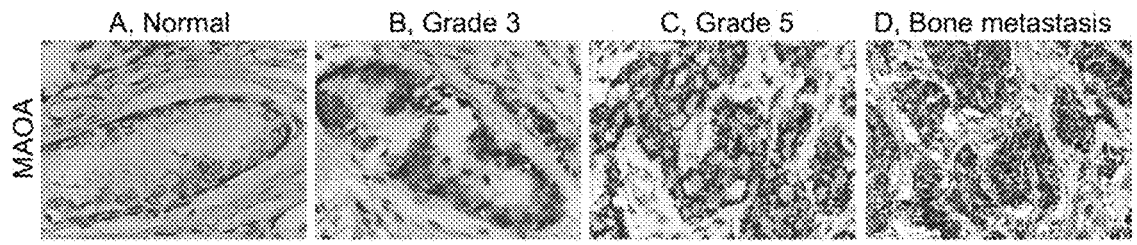
FIG. 13 shows representative immunohistochemical staining of normal (A), Gleason pattern 3 (B) and 5 (C), and bone-metastatic (D) human prostate adenocarcinoma clinical samples showed increased MAO-A expression in high grade and bone metastatic PCa. Magnifications are ×400 (A-C) and ×200 (D), respectively.

Our preliminary data suggest that MAO-A is closely related to prostate cancer (PCa) metastasis to bone and for the first time demonstrate that MAO-A protein expression was elevated in PCa bone metastasis relative to normal and low Gleason grade cancerous epithelium (FIG. 13).

Figure 14:
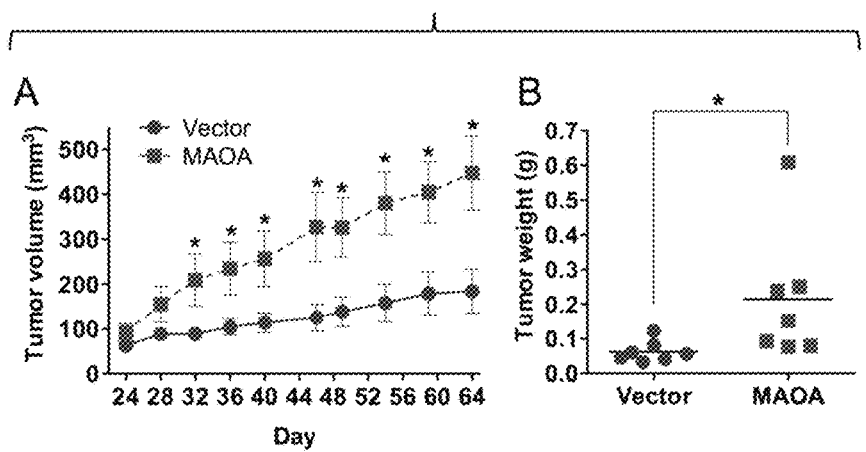
FIG. 14 MAO-A determines the growth of human PCa tumor xenografts in viva Left panel (A-B), stable overexpression of MAO-A in human PC-3 cells, which exhibit limited MAO-A expression at baseline, enhanced the growth of tumor xenografts (A) and tumor weight (B) in athymic nude mice (N=8). Right panel (C-D), shMAO-A knockdown (KD) of MAO-A in human ARCaPM cells eliminated the growth of tumor xenografts (C-D) in athymic nude mice (N=5). shCon and shMAO-A, WT and MAO-A-KD cells. *, $p<0.05$, **, $p<0.01$.
Figure 14:
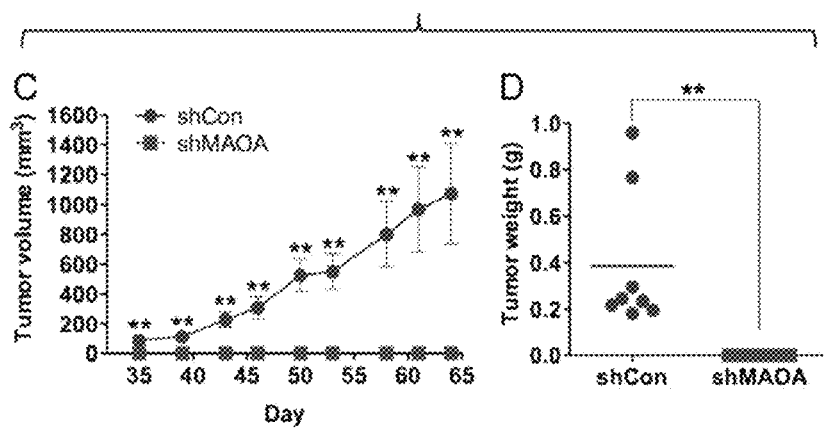

Manipulation of levels of MAO-A expression in human bone-metastatic PC-3 and ARCaP$_M$ PCa cells resulted in altered tumor growth in mice. PC-3 cells overexpressing wild-type MAO-A enhanced its growth whereas ARCaP$_M$ cells with specific lentiviral shRNA-mediated silencing completely abrogated the growth of this invasive and bone-metastatic PCa tumor in mice (FIG. 14). These results raise the possibility that MAO-A is an ideal therapeutic target for the treatment of PCa tumors with high propensity for bone and visceral organ metastases.

Figure 15:
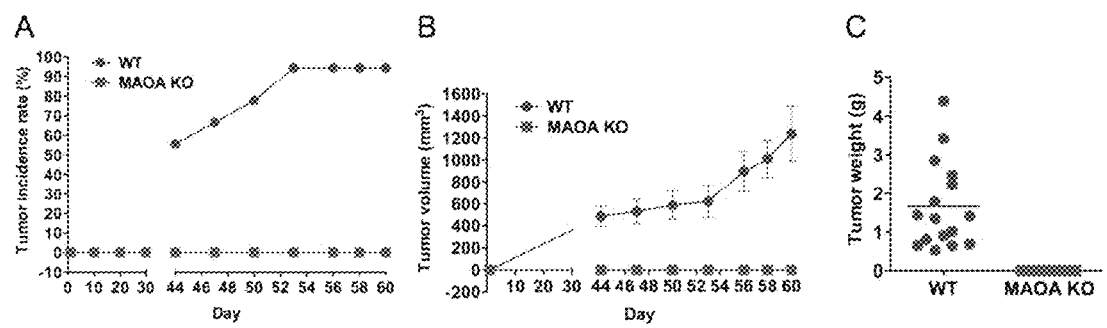
FIG. 15 shows effect of host MAO-A on prostate cancer growth. $1 \times 10^5$ of murine prostate carcinoma TRAMPC-2 cells were subcutaneously injected into WT (N=6) and MAOA KO (N=4) mice, 3 injection sites per mouse. Murine prostate carcinoma TRAMPC-2 (neuroendocrine phenotype), subcutaneously injected into the MAO-A neo mice, showed significantly reduced growth rate of PCa, thereby suggesting a key role that host MAO-A plays in determining the rate of prostate cancer growth. Tumor incidence rate (A) and tumor volume (B) were determined along with tumor progression, and tumor weight (C).

Our experiments with murine prostate carcinoma TRAMPC-2 (neuroendocrine phenotype), subcutaneously injected into the MAOA neo mice, showed significantly reduced growth rate of PCa (FIG. 15), thereby suggesting a key role that host MAOA plays in determining the rate of prostate cancer growth.

Figure 16:
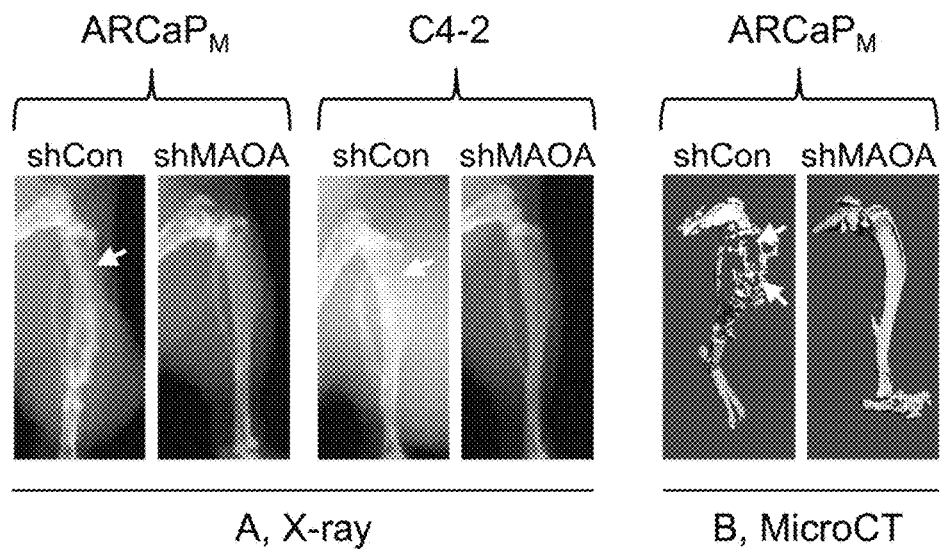
FIG. 16 Representative X-ray (A) and Micro-CT (B) of bone destruction (13-19 week) in mice intratibially injected with scramble/MAO-A-KD human ARCaPM or C4-2 Pea cells. White arrows point to osteolytic lesions.

Specifically in the bone microenvironment, knockdown of MAO-A in two castration-resistant human PCa cell lines, ARCaP$_M$ and C4-2, also significantly reduced cancer-induced local bone destruction by osteolytic lesions (FIG. 16).

Figure 17:
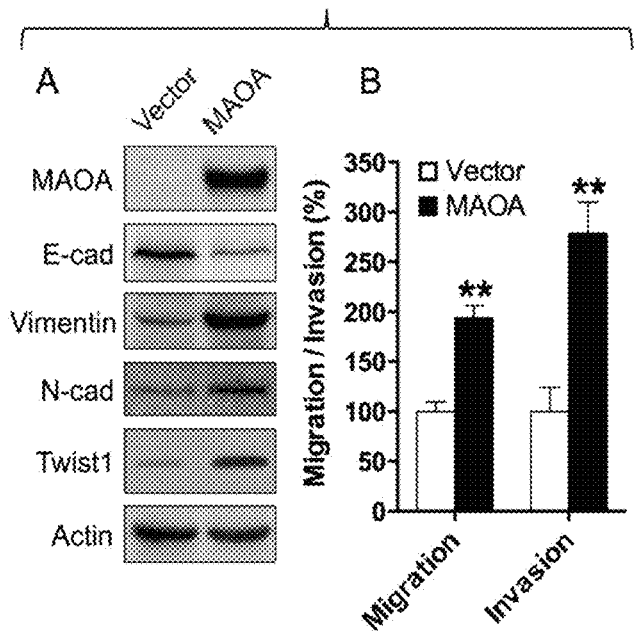
FIG. 17 MAO-A induces EMT in human PCa cells. Left panel (A-B), overexpression of MAO-A in PC-3 cells repressed E-cadherin and up-regulated Vimentin, N-cadherin and Twist1 (A), and increased cell migration and invasion (B). Right panel (C-E), shRNA knockdown of MAOA in ARCaPM cells increased E-cadherin and down-regulated N-cadherin and Twist1 (C), reduced cell migration and invasion (D), and changed cell morphology (E). **, p<0.01. Magnifications are 200×.
Figure 17:
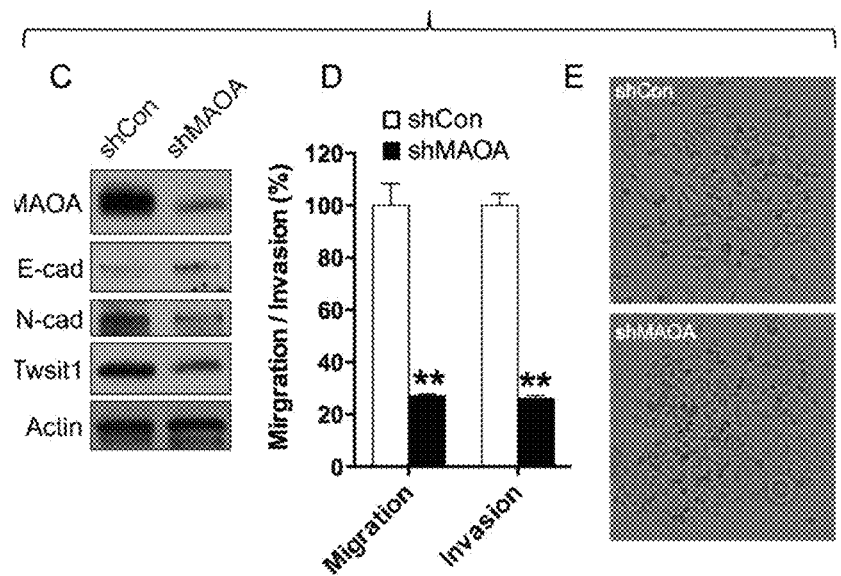

Mechanistically, MAO-A was found to induce epithelial-to-mesenchymal transition (EMT) in human PCa cells, by promoting the loss of E-cadherin expression (an epithelial marker), up-regulation of Vimentin-N-cadherin (mesenchymal markers) and increased migration and invasion in PC-3 cells (FIG. 17A-B); conversely, MAOA knockdown impeded EMT in human ARCaP$_M$ cells (FIG. 17C-E). Activation of the EMT program can direct the local growth and distant dissemination of PCa cells to skeletons and soft tissues. These data suggest that MAO-A expression and its downstream signaling axes might be highly relevant to the development of metastatic PCa and its associated EMT phenotypes.

Figure 18:
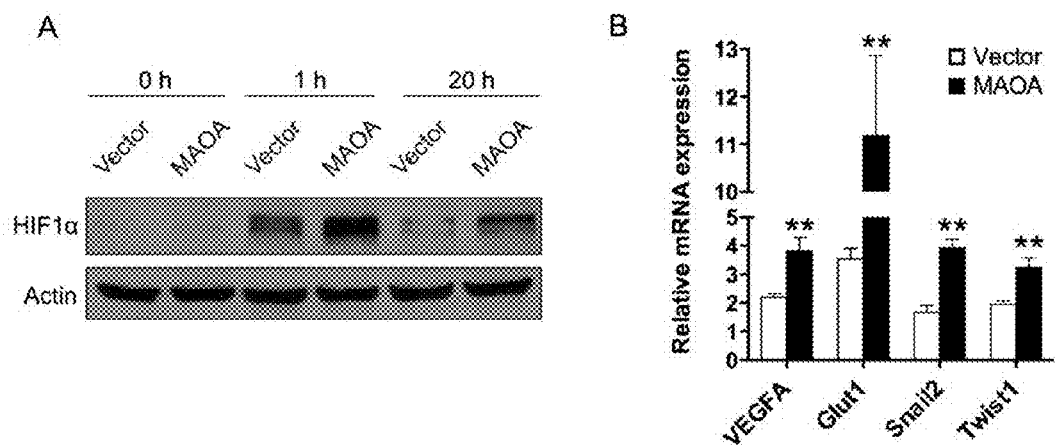
FIG. 18 MAO-A enhances HIF1α expression in human PCa cells. (A) Overexpression of MAO-A increased HIF1α levels under hypoxia (0.5% O2), and (B) activated HIF1α-regulated VEGFA, glucose transporter 1 (Glut1), Snail2 and Twist1 mRNA expression in response to 24-h hypoxia in PC-3 cells. Relative mRNA expression was all normalized with control PC-3 cells under normoxia. **, p<0.01.

We also observed that overexpression of MAO-A enhanced hypoxia-inducible factor 1α (HIF1α) expression, and select HIF1α target genes known to promote PCa progression and metastasis, such as VEGF and EMT-promoting genes (Snail2 and Twist1), are also influenced by MAO-A in PCa cells (FIG. 18). Hypoxia increases tumor angiogenesis and survival responses as well as invasion and metastasis through the up-regulation of HIF1α-dependent relevant genes. Chronic hypoxia, a hallmark of many solid tumors, often in conjugation with elevated levels of reactive oxygen species, has been suggested to affect each step of the metastasis process, from the initial EMT to the ultimate organotropic colonization. Thus, this data further provides important mechanistic insights into the roles of MAO-A in mediating human PCa metastasis to bone and other soft tissues.

Figure 19:
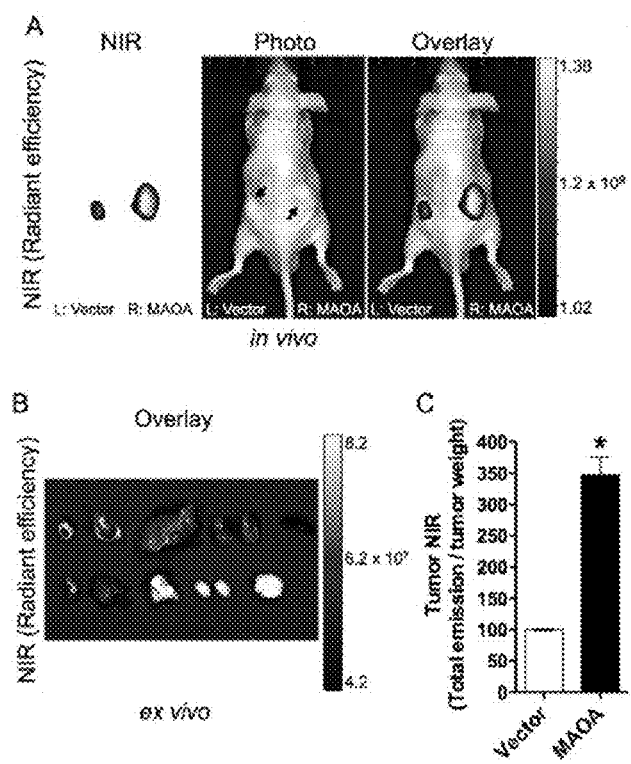
FIG. 19 MAO-A enhanced NIR dye uptake in PC-3 tumor xenografts. (A) Representative in vivo MHI-148 NIR imaging (i.p. injection, 10 nmol/20 g) of nude mice subcutaneously implanted with control (left flank) and MAO-A-overexpressing (right flank) PC-3 cells. Arrows point to tumor xenografts. (B) Tumor tissues but not organs displayed strong signals by ex vivo NIR imaging. (C) Quantitation of tumor NIR intensity in (A) by determining total emission divided by tumor weight (5 mice). *, p<0.05.
Figure 20:
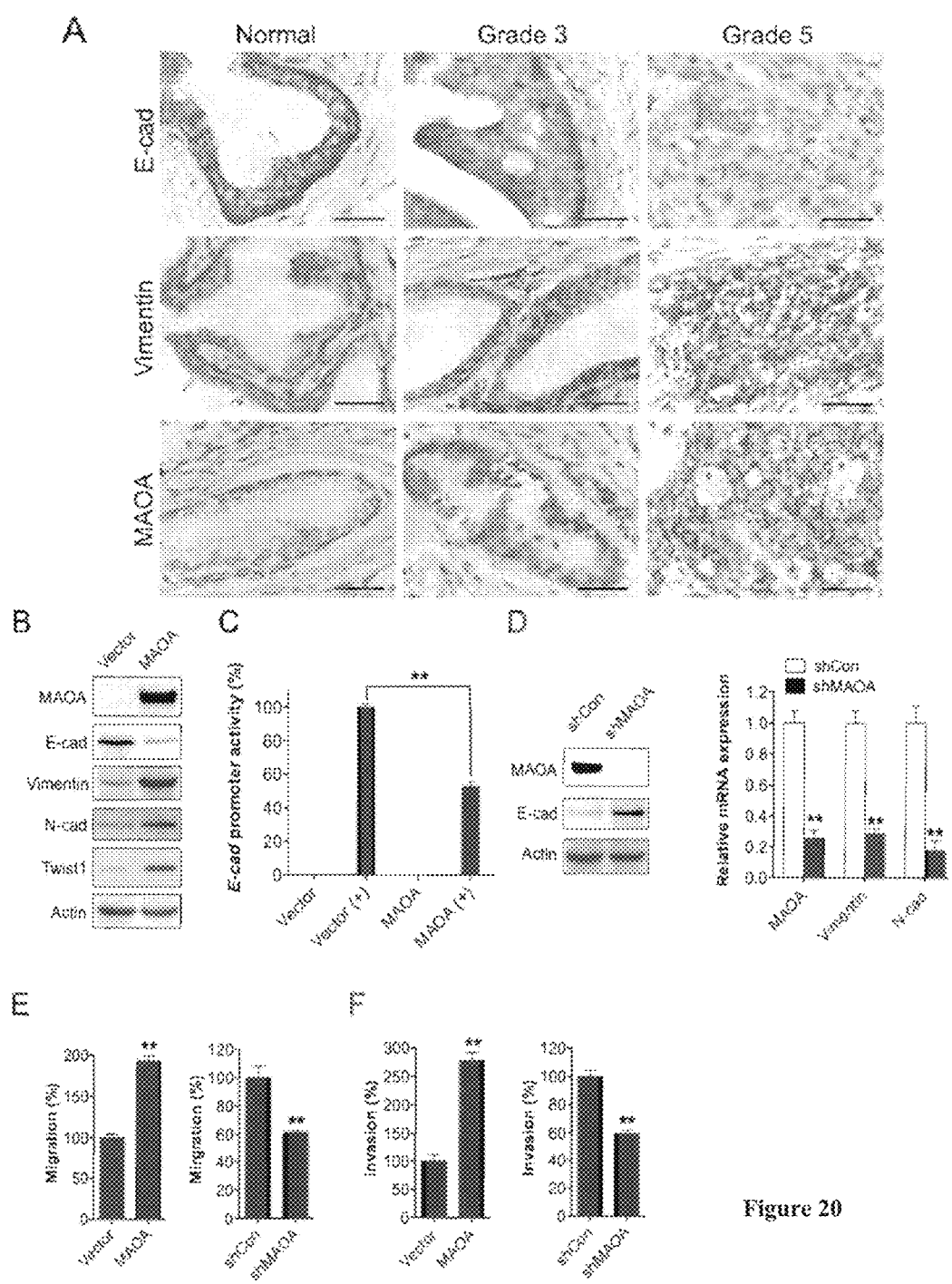
FIG. 20 (A) shows immunohistochemistry of E-cad, Vim and MAO-A in human patient samples of normal, G3 and G5. (B) shows Western blot of MAO-A, E-cad, Vim, N-cad and Twist1 in MAO-A overexpressing PC-3 cells. (C) shows Luc assay of E-cad promoter in control and MAO-A overexpressing PC-3 cells. (D) shows Western blot of MAO-A and E-cad in MAO-KD LNCaP cells, real-time PCR of Vim and N-cad in MAO-A-KD LNCaP cells. (E) shows migration assays of MAO-A-manipulated PC-3 and LNCaP cells. (F) shows invasion assays of MAO-A-manipulated PC-3 and LNCaP cells.
Figure 21:
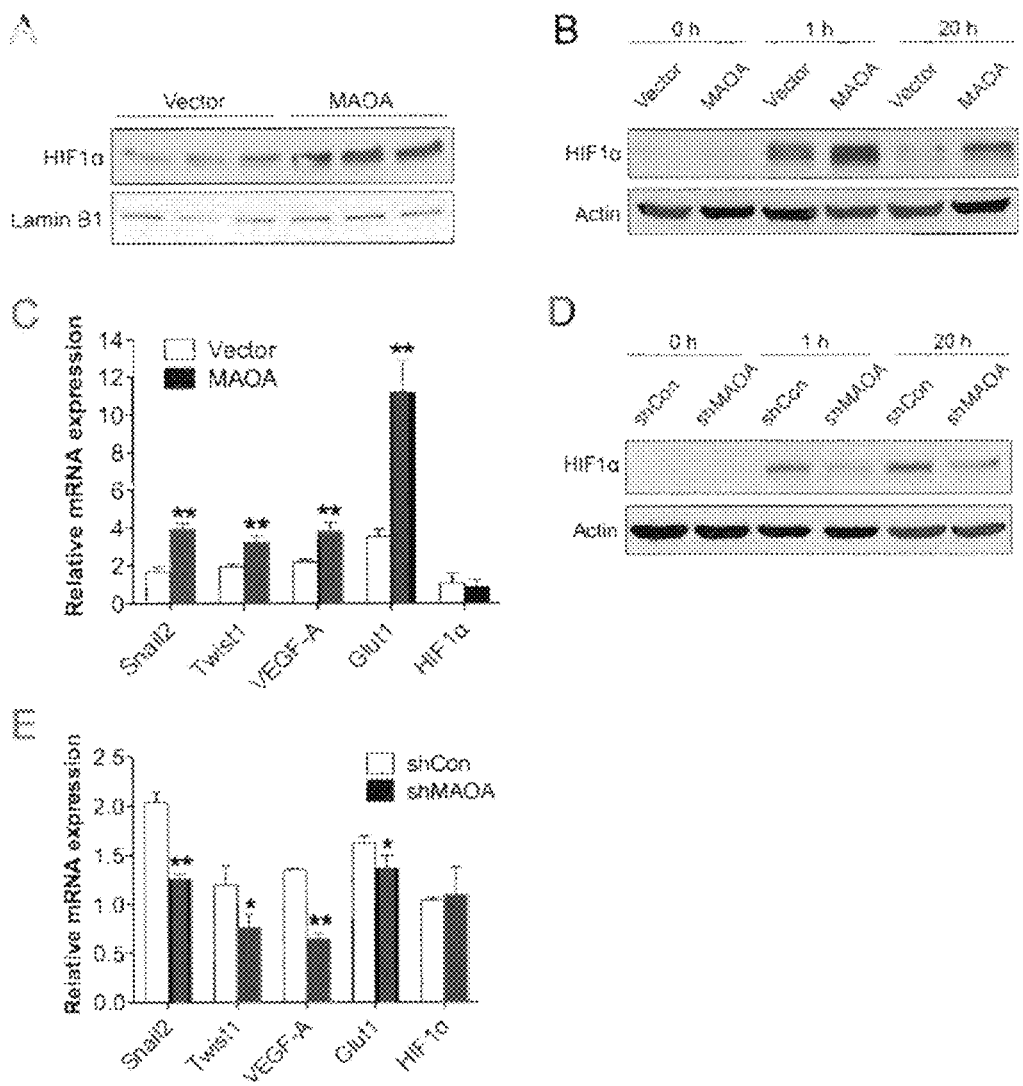
FIG. 21 (A) shows Western blot of nuclear HIF1α in MAO-A overexpressing PC-3 cells. (B) shows Western blot of HIF1α in MAO-A overexpressing PC-3 cells in a time-dependent manner. (C) shows real-time RT-PCR of Snail2, Twist1, VEGFA, Glut1 and HIF1α in MAO-A overexpressing PC-3 cells. (D) Western blot of HIF1α, in MAO-A-KD LNCaP cells in a time-dependent manner. (E) shows real-time RE-PCR of Snail2, Twist1, VEGFA, Glut1 and HIF1α in MAO-A-KD LNCaP cells.
Figure 22:
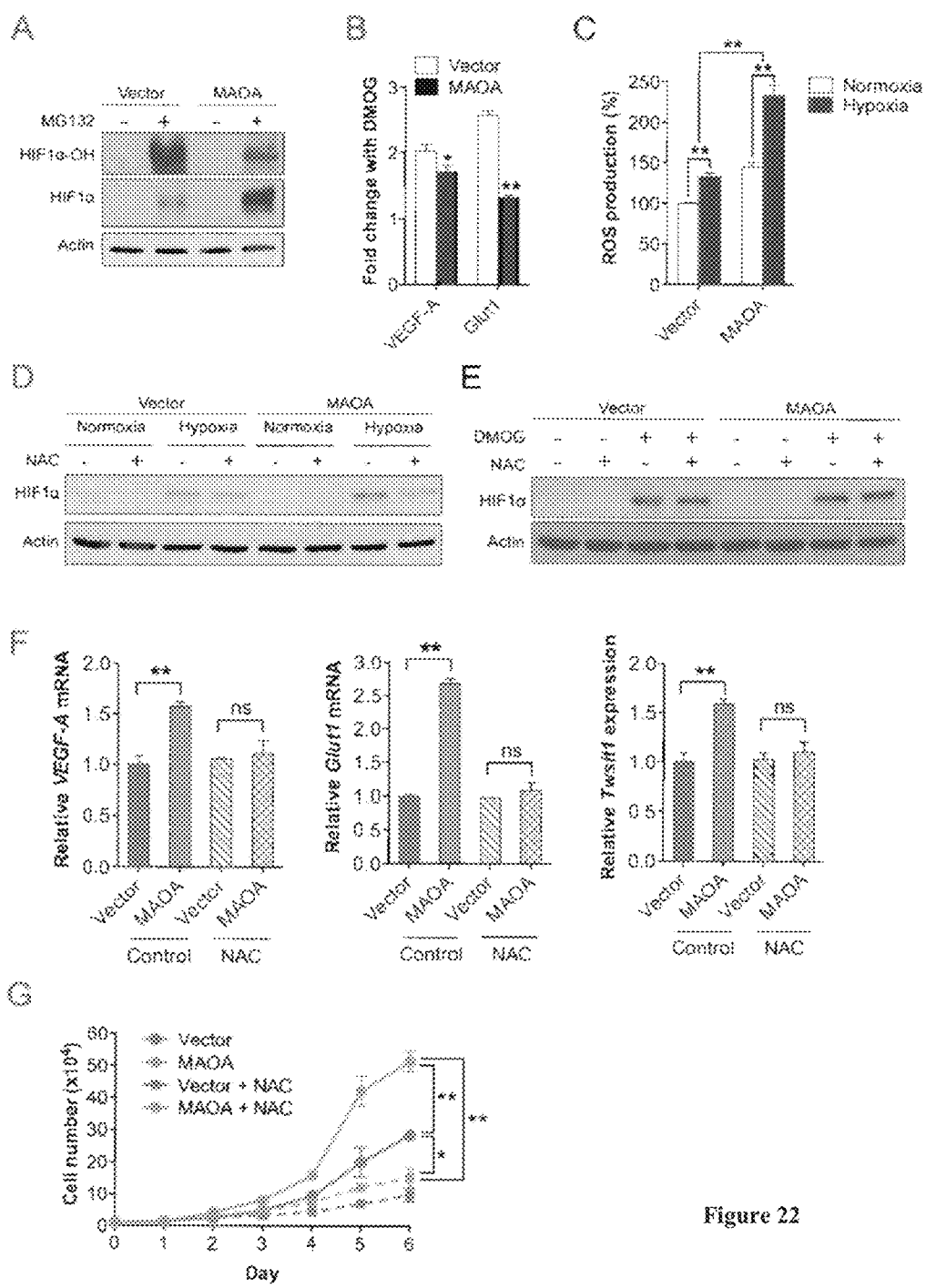
FIG. 22 (A) Western blot of HIF1α-OH and HIF1α, in MAO-A overexpressing PC-3 cells with the treatment of MG-132. (B) real-time PCR of VEGFA and Glut1 in MAO-A overexpressing PC-3 cells of DMOG treatment. (C) FACS of ROS measurement in MAO-A expressing PC-3 cells under hypoxia. (D) Western blot of HIF1α in MAO-A overexpressing PC-3 cells of NAC treatment under hypoxia. (E) real-time RT-PCR of Twist1, VEGFA and Glut1 in MAO-A overexpressing PC-3 cells of NAC treatment under hypoxia. (F) shows Western blot of HIF1α in MAO-A overexpressing PC-3 cells of both NAC and DMOG treatment. (G) shows exemplary cells proliferation curves of MO-A overexpressing PC-3 cells under the treatment of NAC.
Figure 23:
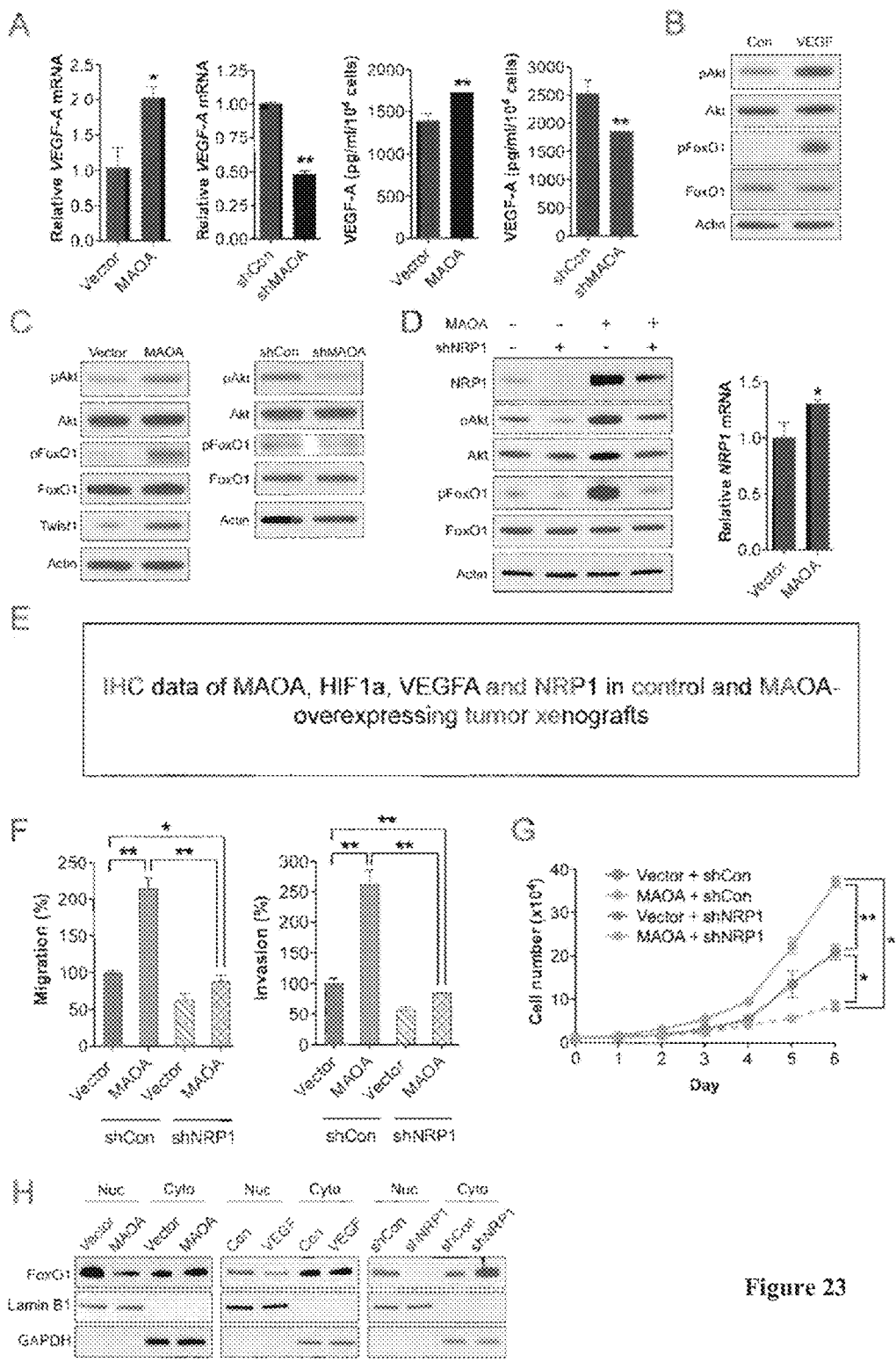
FIG. 23 (A) shows real-time RT-PCR and ELISA of VEGF in MAO-A manipulated PC-3 and LNCaP cells. (B) shows Western blot of pAkt and pFoxO1 in PC-3 cells with VEGF treatment. (C) shows Western blot of pAkt and pFoxO1 in MAO-A manipulated PC-3 and LNCaP cells. (D) Western blot of NRP-1, pAkt and pFoxO1 in MAO-A overexpressing/NRP-1-KD PC-3 cells. (E) shows immunohistochemistry of H&E, VEGF and NRP-1 in MAO-A overexpressing PC-3 tumor xenografts. (F) shows migration and invasion assays of MAO-A overexpressing and NRP-1-KD PC-3 cells. (G) shows exemplary cell proliferation curves of MAO-A overexpressing PC-3 and NRP-1-KD PC-3 cells. (H) shows Western blot of nuclear FoxO1 in MAO-A overexpressing PC-3 cells, PC-3 cells with VEGF treatment, and NRP-1-KD PC-3 cells.
Figure 24:
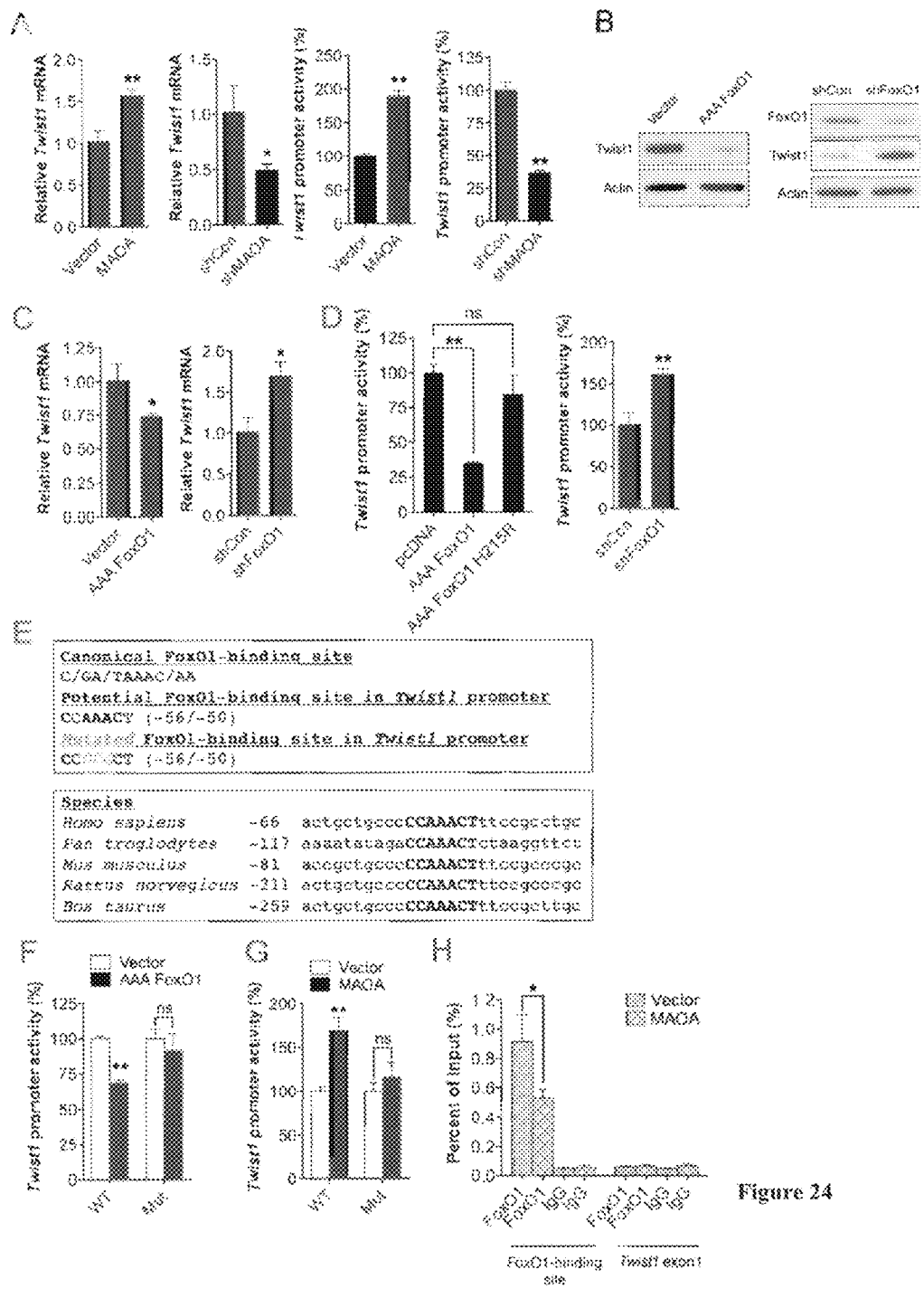
FIG. 24 (A) real-time RT-PCR and luc assay of Twist1 mRNA or promoter in MAO-A manipulated PC-3 and LNCaP cells. (B) Western blot and real-time RT-PCR of Twist1. in FoxO1manipulated PC-3 cells. (C) shows luc assay of Twist1 promoter with WTIH215R AAA FoxO1 construct in PC-3 cells. (D) shows characterization of a FoxO1-binding site in Twist1 promoter across different species. (E) shows luc assay of WT/Mut Twist1 promoter with FoxO1 construct in PC-3 cells. C/GA/TAAAC/AA is SEQ ID NO:6. actgctgcccCCAAACTttccgcctgc is SEQ ID: NO:7. aaaatatagaCCAAACTctaaggttct is SEQ ID: NO:8. accgctgcceCCAAACTttccgcccgc is SEQ ID: NO:9. actgct-gcccCCAAACTttccgcccgc is SEQ ID: NO:10. actgctgc-ccCCAAACTttccgcttgc is SEQ ID: NO:11. (F) shows luc assay of WT/Mut Twist1 promoter in MAO-A overexpressing PC-3 cells. (G) ChIP assay of the FoxO1-binding site in MAO-A overexpressing PC-3 cells. (H) shows a comparison of knock-down versus MOA-A inhibition.
Figure 25A:
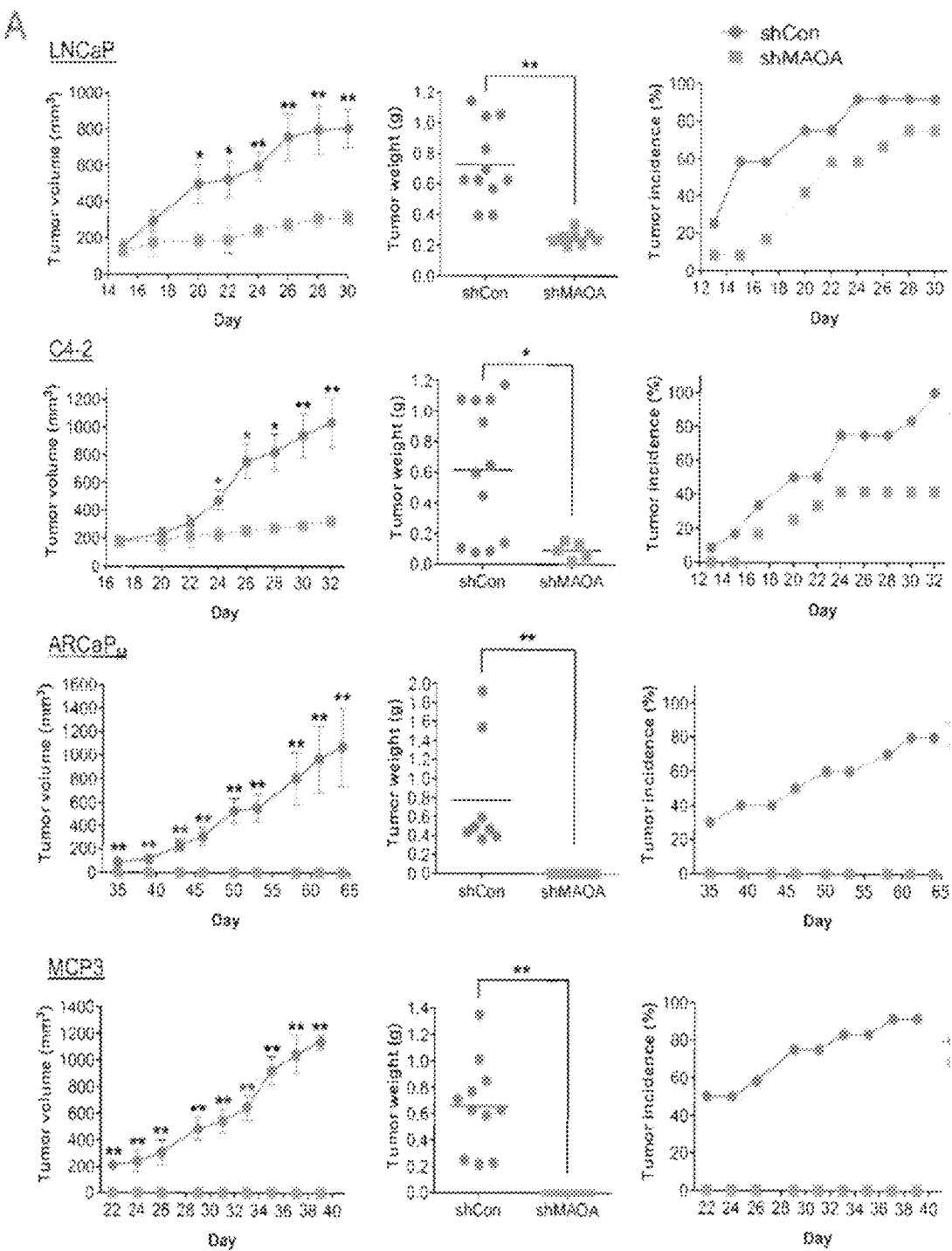
FIG. 25A-E (A) shows tumor incidence, tumor volume and tumor weight of MAO-A-KD LNCaP, C4-2, ARCaP$_m$ and MCP3 tumor xenograft. (B) shows MAO-A activity of MAO-A-KD LNCaP and C4-2 tumor xenografts. (C)-(E) shows immunohistochemistry of H&E, MAO-A, E-cad, Vim, HIF1α, and VEGF in MAO-A-KD LNCaP and C4-2 tumor xenografts. (D) shows tumor mitochondrial ROS measurement in MAO-A-KD LNCaP and C4-2 tumor xenografts.
Figure 25B:
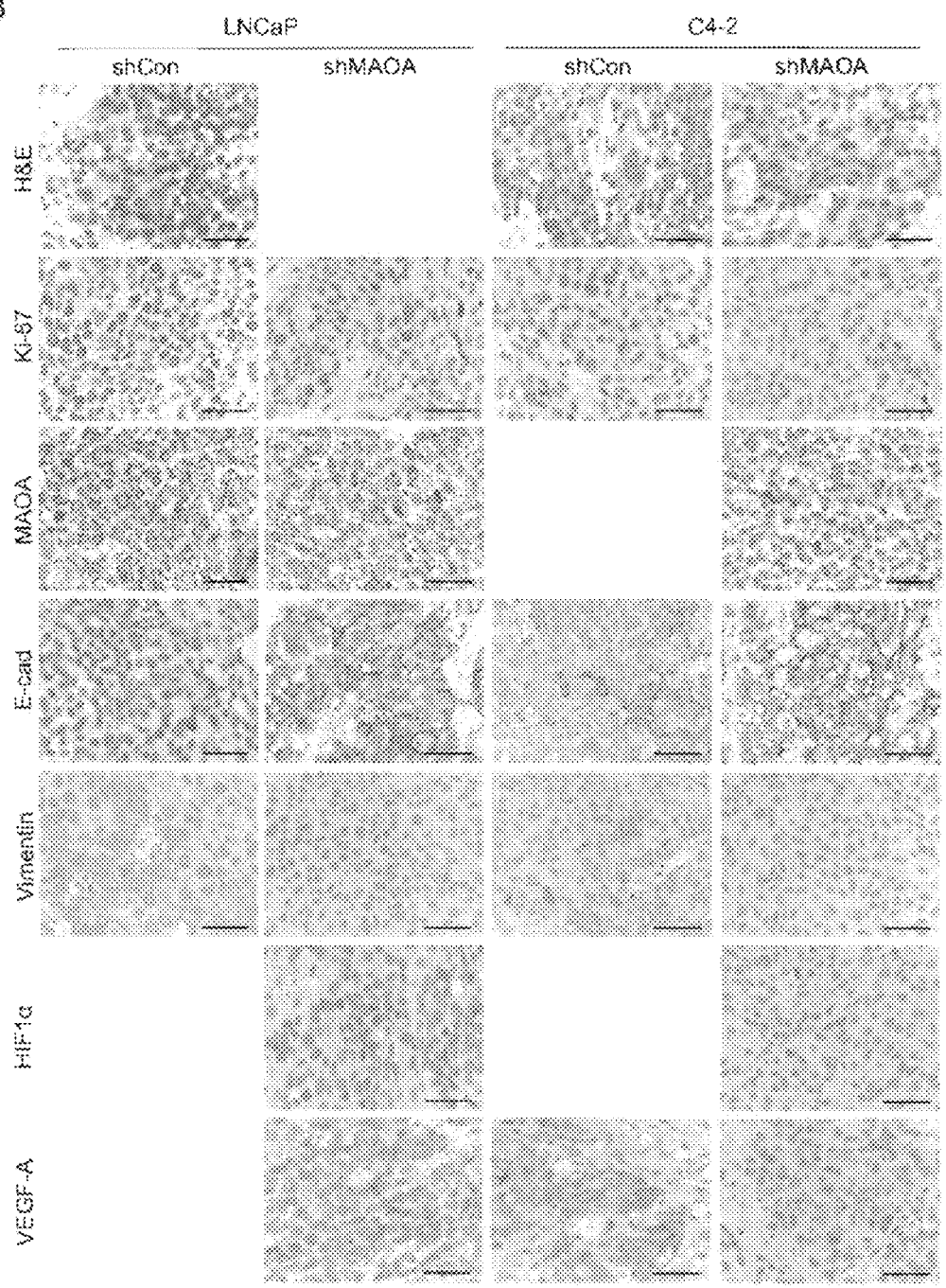
Figures 25C, 25D, 25E:
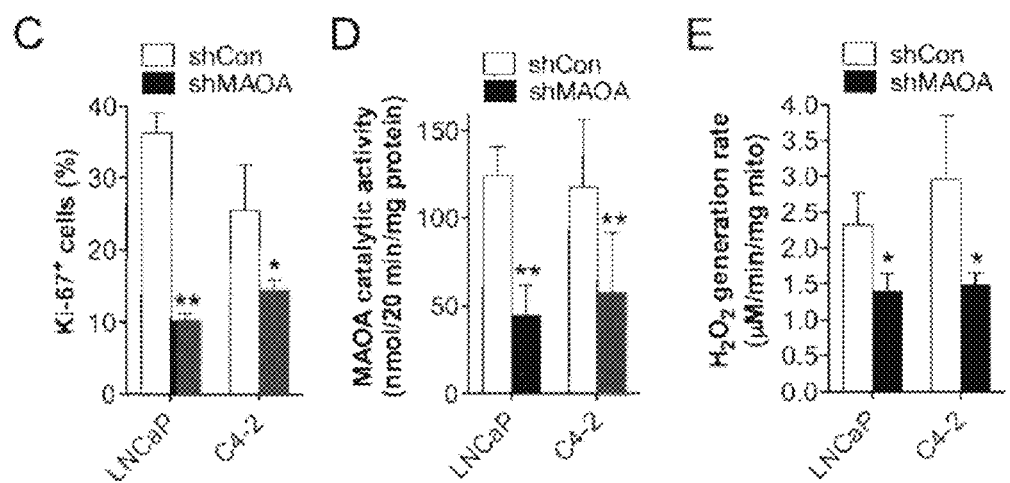
Figure 26:
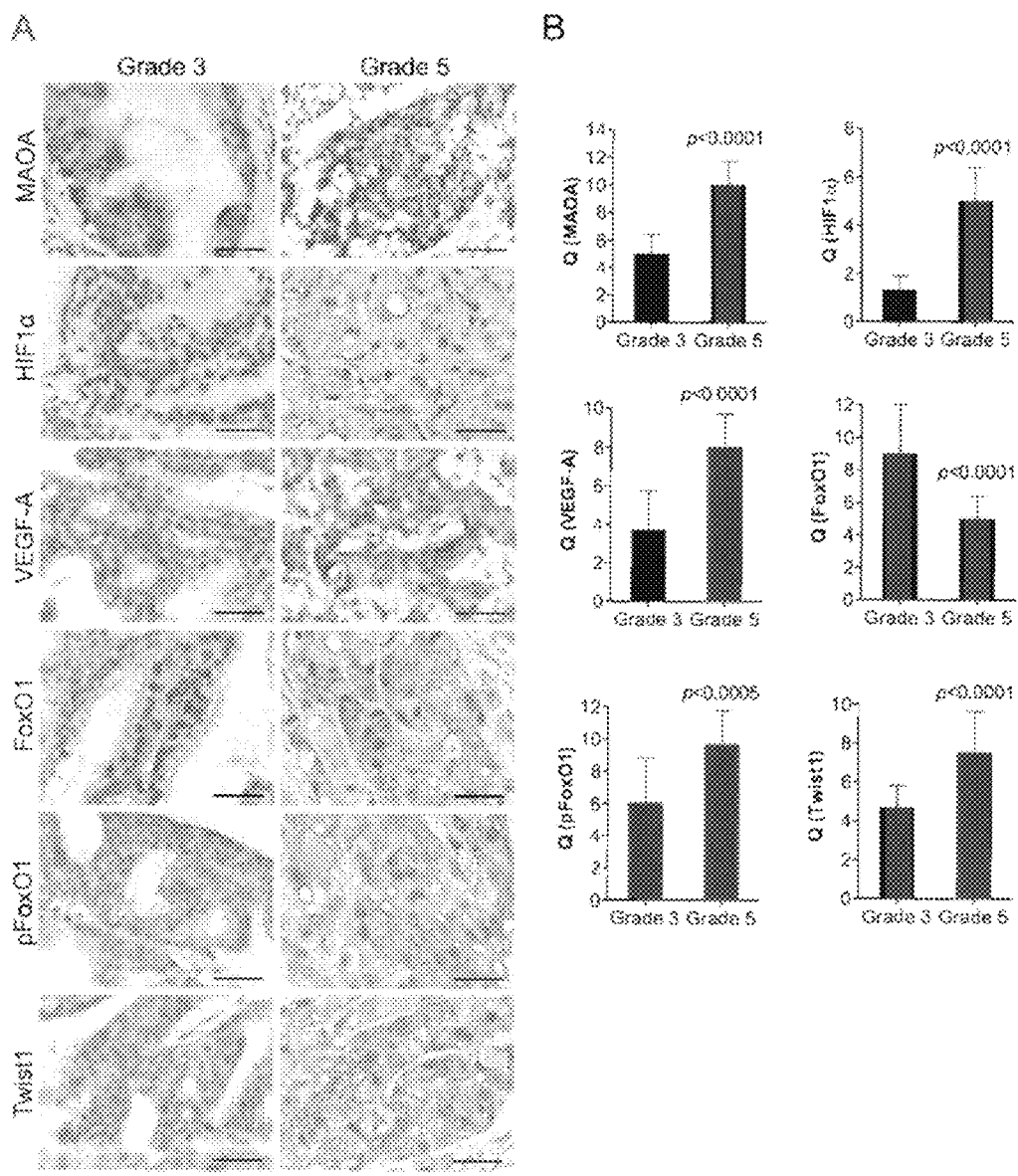
FIG. 26 (A) shows immunohistochemistry of MAO-A, HIF1α, VEGFA, FoxO1, pFoxO1 and Twist1 in human patient samples of G3 and G5. (B) shows statistical analysis of immunohistochemistry data.

A class of fluorescent heptamethine cyanines with near-infrared (NIR) emission maxima, such as MHI-148 dye, which has been identified recently, are non-toxic and have dual functions as tumor-specific targeting and imaging modalities. These dyes, partially mediated by hypoxia, are specifically retained in cancer but not normal cells, and also in tumor xenografts as well as spontaneous tumors in transgenic mice. We have shown enhanced uptake of MHI-148 NIR dye in MAO-A-overexpressing PC-3 tumor xenografts (FIG. 19). This would allow the development and validation of novel PCa-seeking MAO-A inhibitors with acquired synergistic tumor-targeting abilities as new agents for PCa therapies with minimal systemic host toxicity.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are incorporated herein by reference:

1. Bortolato, M., Chen, K., and Shih, J. C. (2008) *Advanced Drug Delivery Reviews* 60, 1527-1533
2. Shih, J, C., Chen, K., and Ridd, M. J. (1999) *Annual Review of Neuroscience* 22, 197-217
3. Josson, S., Nomura, T., Lin, J. T., Huang, W. C., Wu, D. Q., Zhau, H. E., Zayzafoon, M., Weizmann, M. N., Gururajan, M., and Chung, L. W. K. (2011) *Cancer Research* 71, 2600-2610
4. Trachootham, D., Alexandre, J., and Huang, P. (2009) *Nature Reviews Drug Discovery* 8, 579-591
5. Peehl, D. M., Coram, M., Khine, H., Reese, S., Nolley, R., and Zhao, H. J. (2008) *Journal of Urology* 180, 2206-2211
6. Zhao, H. J., Flamand, V., and Peehl, D. M. (2009) *Bmc Medical Genomics* 2, —
7. Flamand, V., Zhao, H. J., and Peehl, D. M. (2010) *Journal of Cancer Research and Clinical Oncology* 136, 1761-1771
8. True, L., Coleman, I., Hawley, S., Huang, C. Y., Gifford, D., Coleman, R., Beer, T. M., Gelmann, E., Datta, M., Mostaghel, E., Knudsen, B., Lange, P., Vessella, R., Lin, D., Hood, L., and Nelson, P. S. (2006) *Proceedings of the National Academy of Sciences of the United States of America* 103, 10991-10996
9. De Colibus, L., Li, M., Binda, C., Lustig, A., Edmondson, D. E., and Mattevi, A. (2005) *Proceedings of the National Academy of Sciences of the United States of America* 102, 12684-12689
10. Ueno, Y., Jose, J., Loudet, A., Perez-Bolivar, C., Anzenbacher, P., Jr., and Burgess, K. (2011) *J Am Chem Soc* 133, 51-55
11. Barth, B. M., Sharma, R., Altinoglu, E. I., Morgan, T. T., Shanmugavelandy, S. S., Kaiser, J. M., McGovern, C., Matters, G. L., Smith, J. P., Kester, M., and Adair, J. H. (2010) *Acs Nano* 4, 1279-1287
12. Altinoglu, E. I., Russin, T. J., Kaiser, J. M., Barth, B. M., Eklund, P. C., Kester, M., and Adair, J. H. (2008) *Acs Nano* 2, 2075-2084
13. Jose, J., Loudet, A., Ueno, Y., Wu, L., Chen, H. Y., Son, D. H., Barhoumi, R., Burghardt, R., and Burgess, K. (2011) *Org Biomol Chem* 9, 3871-3877

What is claimed is:

1. A compound of the formula:

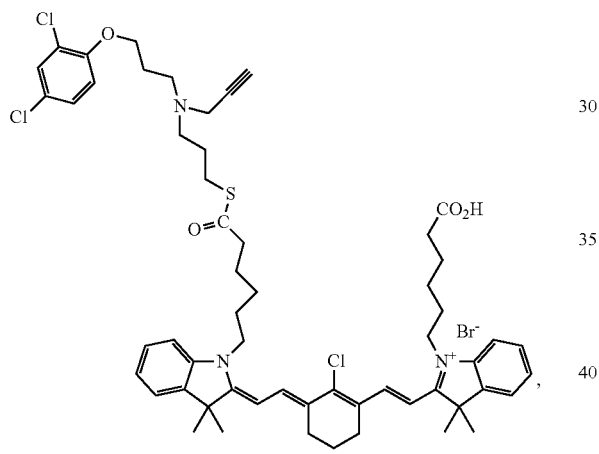

or a pharmaceutically acceptable salt thereof.

2. A pharmaceutical composition useful for treating prostate cancer, comprising the compound of claim 1, and a pharmaceutically acceptable excipient.

3. A method for treating prostate cancer, comprising: administering to a subject having prostate cancer a therapeutically effective amount of the pharmaceutical composition of claim 2.

* * * * *

UNITED STATES PATENT AND TRADEMARK OFFICE
CERTIFICATE OF CORRECTION

PATENT NO. : 9,771,625 B2
APPLICATION NO. : 13/559431
DATED : September 26, 2017
INVENTOR(S) : Shih et al.

Page 1 of 1

It is certified that error appears in the above-identified patent and that said Letters Patent is hereby corrected as shown below:

In the Specification

Please delete the paragraph beginning on Line 17 of Column 1 and ending on Line 21 of Column 1, and replace with the following paragraph:
--This invention was made with government support under DAMD17-03-2-0033, and W81XWH-12-1-0282 awarded by the Defense Health Agency, Medical Research and Development Branch, and P01 CA098912, R01 CA122602, and R01 MH039085 awarded by the National Institutes of Health. The government has certain rights in the invention.--

Signed and Sealed this
First Day of April, 2025

Coke Morgan Stewart
*Acting Director of the United States Patent and Trademark Office*